United States Patent
Montero-Julian et al.

(10) Patent No.: US 8,815,528 B2
(45) Date of Patent: Aug. 26, 2014

(54) METHODS AND SYSTEMS FOR DETECTING MHC CLASS I BINDING PEPTIDES

(75) Inventors: Felix A. Montero-Julian, Marseilles (FR); Sylvain Monseaux, Marseilles (FR)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/029,902

(22) Filed: Feb. 17, 2011

(65) Prior Publication Data

US 2011/0171752 A1 Jul. 14, 2011

Related U.S. Application Data

(63) Continuation of application No. 10/269,473, filed on Oct. 11, 2002, now abandoned.

(51) Int. Cl.
*G01N 33/543* (2006.01)
*G01N 33/566* (2006.01)
*G01N 33/68* (2006.01)

(52) U.S. Cl.
USPC ............ 435/7.5; 435/7.8; 436/501; 436/518; 436/86

(58) Field of Classification Search
None
See application file for complete search history.

(56) References Cited

U.S. PATENT DOCUMENTS

| | | | |
|---|---|---|---|
| 4,017,597 A | 4/1977 | Reynolds | |
| 4,048,298 A | 9/1977 | Niswender | |
| 4,120,945 A | 10/1978 | Gutcho et al. | |
| 4,208,479 A | 6/1980 | Zuk et al. | |
| 4,228,237 A | 10/1980 | Hevey et al. | |
| 4,478,946 A | 10/1984 | Van der Merwe et al. | |
| 4,912,030 A | 3/1990 | Weiss et al. | |
| 5,187,065 A | 2/1993 | Schutzer | |
| 5,514,557 A | 5/1996 | Moghaddam | |
| 5,534,416 A | 7/1996 | Millard et al. | |
| 5,583,031 A | 12/1996 | Stern | |
| 5,599,720 A | 2/1997 | Elkins | |
| 5,635,363 A | 6/1997 | Altman et al. | |
| 5,734,023 A | 3/1998 | Nag et al. | |
| 5,759,774 A | 6/1998 | Hackett et al. | |
| 5,917,018 A * | 6/1999 | Thøgersen et al. ............ 530/350 |
| 5,919,639 A | 7/1999 | Humphreys et al. | |
| 5,965,532 A | 10/1999 | Bachovchin | |
| 6,037,135 A | 3/2000 | Kubo et al. | |
| 6,046,013 A | 4/2000 | Tidey et al. | |
| 6,120,992 A * | 9/2000 | Wagner, Jr. .................. 435/6.11 |
| 6,225,042 B1 | 5/2001 | Cai et al. | |
| 6,270,772 B1 | 8/2001 | Burrows et al. | |
| 6,306,636 B1 * | 10/2001 | Haselkorn et al. ............ 435/232 |
| 6,355,479 B1 | 3/2002 | Webb et al. | |
| 6,413,517 B1 | 7/2002 | Sette et al. | |
| 6,419,931 B1 | 7/2002 | Vitiello et al. | |
| 6,485,913 B1 | 11/2002 | Becker et al. | |
| 6,500,617 B1 * | 12/2002 | Stemmer et al. .................. 506/1 |
| 6,727,093 B2 | 4/2004 | Diamond | |
| 6,992,176 B2 | 1/2006 | Reiter et al. | |
| 2002/0006903 A1 | 1/2002 | Schneck et al. | |
| 2002/0106708 A1 | 8/2002 | Thomas et al. | |
| 2002/0146746 A1 | 10/2002 | Nixon et al. | |
| 2003/0044389 A1 | 3/2003 | Brown et al. | |
| 2003/0044415 A1 | 3/2003 | Savage | |
| 2003/0124513 A1 | 7/2003 | McSwiggen | |
| 2003/0124613 A1 | 7/2003 | Hildebrand et al. | |
| 2003/0166057 A1 | 9/2003 | Hildebrand et al. | |
| 2004/0137537 A1 | 7/2004 | Montero-Julian et al. | |
| 2004/0253632 A1 | 12/2004 | Rhode et al. | |
| 2005/0059107 A1 | 3/2005 | Maillere et al. | |
| 2005/0095655 A1 | 5/2005 | Montero-Julian et al. | |
| 2005/0287611 A1 | 12/2005 | Nugent et al. | |
| 2006/0040332 A1 | 2/2006 | Maeurer | |

FOREIGN PATENT DOCUMENTS

| | | | |
|---|---|---|---|
| EP | 0 958 834 A1 | 11/1999 | |
| EP | 1 138 766 A2 | 10/2001 | |
| JP | 4-505401 | 9/1992 | |
| JP | 6-506056 | 7/1994 | |
| WO | WO 86/05809 | * 10/1986 | ............. C12P 21/00 |
| WO | WO 92/07952 A1 | 5/1992 | |
| WO | WO 94/11738 A1 | 5/1994 | |
| WO | WO 95/04817 A1 | 2/1995 | |
| WO | WO 97/00067 A1 | 1/1997 | |
| WO | WO 97/04085 A1 | 2/1997 | |
| WO | WO 97/09429 A2 | 3/1997 | |
| WO | WO 98/23690 A1 | 6/1998 | |
| WO | WO 99/28748 A2 | 6/1999 | |
| WO | WO 99/50637 A2 | 10/1999 | |

(Continued)

OTHER PUBLICATIONS

Sun et al. "Identification of a new HLA-A 0201-restricted T-cell epitope from the tyrosinase-related protein 2 (TRP2) melanoma antigen" International Journal of Cancer vol. 87, Issue 3, pp. 399-404, Aug. 1, 2000.*

Wang et al. "Class I-Restricted Alloreactive Cytotoxic T Lymphocytes Recognize a Complex Array of Specific MHC-Associated Peptides" J Immunol 1998;160;1091-1097.*

Hlavac et al. "Direct detection of peptide-dependent HLA variability by surface plasmon resonance" Mol Immunol. Apr. 1996;33(6):573-82.*

Cull et al. "Biotinylation of proteins in vivo and in vitro using small peptide tags" Methods Enzymol. 326 (2000), pp. 430-440.*

Reid et al. "Production and crystallization of MHC class I B allele single peptide complexes" FEBS Lett. Mar. 25, 1996;383(1-2):119-23.*

(Continued)

*Primary Examiner* — Christine Foster
(74) *Attorney, Agent, or Firm* — Merchant & Gould P.C.

(57) ABSTRACT

The present invention is based on the discovery that MHC heavy chain monomers immobilized to a solid surface are still capable of forming detectable conformational epitopes and being detected by conformation-dependent antibodies. Methods for detecting peptide binding to HLA monomers, and methods for measuring the relative degree of binding between two MHC-binding peptides as well as a method of measurement for the rate of dissociation of peptides from MHC complexes are provided. The present invention also provides systems and kits useful for conducting the methods of the present invention.

15 Claims, 18 Drawing Sheets

(56) References Cited

FOREIGN PATENT DOCUMENTS

| | | | |
|---|---|---|---|
| WO | WO 00/15665 | | 3/2000 |
| WO | WO 00/25813 A1 | | 5/2000 |
| WO | WO 00/70023 | * | 11/2000 ............... C12N 5/06 |
| WO | WO 01/90747 A2 | | 11/2001 |
| WO | WO 02/44327 A2 | * | 6/2002 |
| WO | WO 02/072631 A2 | | 9/2002 |
| WO | WO 03/040299 A2 | | 5/2003 |
| WO | WO 2004/094458 A2 | | 11/2004 |
| WO | WO 2005/010026 A2 | | 2/2005 |

OTHER PUBLICATIONS

Parham et al. "Use of a monoclonal antibody (W6/32) in structural studies of HLA-A,B,C, antigens" J Immunol. Jul. 1979;123(1):342-9.*

Harlow, E. and Lane, D., Antibodies: A Laboratory Manual (1988) Cold Spring Harbor Laboratory Press, Cold Spring Harbor, NY, pp. 555-556.*

Steinert et al. "Improved immunological assays using Ni-NTA HisSorb Strips", Qiagen News Issue 2 (1997), pp. 12-15, retrieved from http://www.qiagen.com/literature/qiagennews/0297/972impi.pdf on Feb. 22, 2012.*

Rehm et al. "Matrix-assisted in vitro refolding of *Pseudomonas aeruginosa* class II polyhydroxyalkanoate synthase from inclusion bodies produced in recombinant *Escherichia coli*" Biochem. J. (2001) 358, 263-268.*

Suter et al. "The immunochemistry of sandwich ELISAs. II. A novel system prevents the denaturation of capture antibodies" Immunol Lett. Nov. 3, 1986;13(6):313-6.*

Maggio, Edward T., Enzyme Immunoassay, ISBN 0-8493-5617-2, 1980, pp. 186-187.

"2006 Annual Immune Epitope Database and Discovery Workshop Meeting Report Executive Summary," at *The Third Annual Immune Epitope Database and Discovery Workshop* held on Nov. 7 and 8, 2006 in North Bethesda, Maryland, 3 pages (Jan. 2007).

Alexander, J., et al., "Derivation of HLA-A 11/$K^b$ Transgenic Mice: Functional CTL Repertoire and Recognition of Human A11-Restricted CTL Epitopes,", *J. Immunology* 159:4753-4761, The American Association of Immunologists, Bethesda, MD USA (1997).

Arnold, P.Y. et al., "The Majority of Immunogenic Epitopes Generate $CD4^+$T Cells That Are Dependent on MHC Class II-Bound Peptide-Flanking Residues," *J. Immunol.* 169:739-749, The American Association of Immunologists (Jul. 2002).

Baumann, S., et al., "Indirect immobilization of recombinant proteins to a solid phase using the albumin binding domain of streptococcal protein G and immobilized albumin," *J. Immunol. Methods* 221:95-106, North-Holland Pub. Co. (1998).

Belmares, M.P. et al., "Structural Factors Contributing to DM Susceptibility of MHC Class II/Peptide Complexes," *J. Immunol.* 169:5109-5117, The American Association of Immunologists (Nov. 2002).

Bercovici, N. et al., "New Methods for Assessing T-Cell Responses," *Clin. Diagn. Lab. Immunol.* 7:859-864, American Society for Microbiology (2000).

Boder, E.T. et al., "Yeast Surface Display of a Noncovalent MHC Class II Heterodimer Complexed with Antigenic Peptide," *Biotechnol. Bioeng.* 92:485-491, Wiley (Nov. 2005).

Bodinier, M. et al., "Efficient detection and immunomagnetic sorting of specific T cells using multimers of MHC class I and peptide with reduced CD8 binding," *Nat Med.* 6:707-710, Nature Publishing Company (2000).

Burgess, W.H., et al., "Possible Dissociation of the heparin-binding and Mitogenic Activities of Heparin-binding (Acidic Fibroblast) Growth Factor-I from Its Receptor-binding Activities by Site-directed Mutagenesis of a Single Lysine Residue," *J. Cell Biol.* 111:2129-2138, The Rockefeller University Press (1990).

Butler, J.E., "Enzyme-Linked Immunosorbent Assay," in *Immunochemistry*, van Oss, C.J., and van Regenmortel, M.H.V., eds., M. Dekker, New York, NY, pp. 774-775 (1994).

Butler, J.E., "Solid Supports in Enzyme-Linked Immunosorbent Assay and Other Solid-Phase Immunoassays," in *Methods in Molecular Medicine*, vol. 94: *Molecular Diagnosis of infectious Diseases*, Decker, J., and Reischl, U, eds., Humana Press Inc., Totowa, NJ, p. 333-372 (Dec. 2003).

Butler, J.E. et al., "The Immunochemistry of Sandwich ELISAs—VI. Greater Than 90% of Monoclonal and 75% of Polyclonal Anti-Fluorescyl Capture Antibodies (CAbs) Are Denatured by Passive Adsorption," *Mol. Immunol.* 1165-1175, Pergamon Press (1993).

Buus et al. *Current Opinion in Immunology*, 11: 209-213 (1999).

Buus, S. et al., "The Relation Between Major Histocompatibility Complex (MHC) Restriction and the Capacity of Ia to Bind Immunogenic Peptides," *Science* 235:1353-1358, American Association for the Advancement of Science (1987).

Call, ME. et al., "Stoichiometry of the T-cell receptor-CD3 complex and key intermediates assembled in the endoplasmic reticulum," *EMBO.J.* 23:2348-2357, Oxford University Press (Jun. 2004).

Call, M.E., and Wucherpfennig, K.W., "The T Cell Receptor: Critical Role of the Membrane Environment in Receptor Assembly and Function," *Annu. Rev. Immunol.* 23:101-125, Annual Reviews (Apr. 2005).

Carbone, F.R., and Bevan, M.J., "Chapter 18: Major Histocompatibility Complex Control of T Cell Recognition," in *Fundamental Immunology $2^{nd}$ Ed..*, Paul, W.E., ed., Raven Press Ltd., New York, NY, pp. 541-567 (1989).

Cason, J., et al. "Analysis of human lymphocyte transformation responses to graded doses of T cell mitogens by curve fitting," *J. Immunol. Methods* 102:109-117, North-Holland Publishing Co. (1987).

Celis, E., et al., "Induction of anti-tumor cytotoxic T lymphocytes in normal humans using primary cultures and synthetic peptide epitopes," *Proc. Natl. Acad. Sci. U.S.A.* 91:2105-2109, National Academy of Sciences (1994).

Chersi et al., "Polystyrene Beads Coated with Antibodies Directed to HLA Class I Intracytoplasmic Domain: The Use in Quantitative Measurement of Peptide-HLA Class I Binding by Flow Cytometry," *Human Immunology*, 61:1298-1306 (2000).

Constantin, C.M. et al., "Major Histocompatibility Complex (MHC) Tetramer Technology: An Evaluation," *Biol. Res. Nurs.* 4:115-127, Sage Publications, Inc. (Oct. 2002).

Denkberg, G. et al., "Critical Role for CD8 in Binding of MHC Tetramers to TCR: CD8 Antibodies Block Specific Binding of Human Tumor-Specific MHC-Peptide Tetramers to TCR," *The Journal of Immunology* doned, The American Association of Immunologists, Bethesda, MD USA (Jul. 2001).

Denkbero, G. et al., "Direct visualization of distinct T cell epitopes derived from a melanoma tumor-associated antigen by using human recombinant antibodies with MHC restricted T cell receptor-like specificity," *PNAS* 99:9421-9426, Proceedings of the National Academy of Sciences, Washington, DC USA (2002).

Denkberg, G. et al., "Recombinant human single-chain MHC-peptide complexes made from *E. coli* by in vitro refolding: functional single-chain MHC-peptide complexes and tetramers with tumor associated antigens," *.Eur. J. Immunol.* 30:3522-3532, Wiley-VCH Verlag GmbH, Wiley, Hoboken, NJ USA (2000).

Dornmair, K. et al., "Structural Intermediates in the Reactions of Antigenic Peptides with MHC Molecules," *Cold Spring Harb. Symp. Quant. Biol.* 54:409-416, Cold Spring Harbor Laboratory Press (1989).

Du Pasquier, R.A. et al., "Low Frequency of Cytotoxic T Lymphocytes against the Novel HLA-A 0201-Restricted JC Virus Epitope $VP1_{p36}$ in Patients with Proven or Possible Progressive Multifocal Leukoencephalopathy," *J. Virol.* 77:11918-11926, American Society for Microbiology (Nov. 2003).

Dutoit, V. et al., "Functional Avidity of Tumor Antigen-Specific CTL Recognition Directly Correlates with the Stability of MHC/Peptide Multimer Binding to TCR," *J. Immunol.* 168:1167-1171, American Association of Immunologists (Feb. 2002).

Eichmuller et al., "A new method for double immunolabelling with primary antibodies from identical species," *J. Immunol. Methods.* 190(2):255-265 (Apr. 1996).

English language abstract of WO 91/12332 A1 , Dated Jul. 8, 2009, two pages.

(56) References Cited

OTHER PUBLICATIONS

European Search Report for European Application No. EP 05 74 5499, completed on Apr. 24, 2008, European Patent Office, The Hague, Netherlands.

Flad et al., "Direct Identification of Major Histocompatibility Complex Class I-Bound Tumor-Associated Peptide Antigens of a Renal Carcinoma Cell Line by a Novel Mass Spectrometric Method," *Cancer Research* 58(24):5803-5811(1998).

Garboczi et al., *Proc. Natl. Acad. Sci. U.S.A.* 69:3429-3433 (1992).

Geluk, A. et al., "Identification of Major Epitopes of *Mycobacterium tuberculosis* AG85B That Are Recognized by HLA-A 0201-Restricted $CD8^+T$ Cells in HLA-Transgenic Mice and Humans," *J. Immunol.* 165:6463-6471, The American Association of Immunologists (2000).

Gerritsma, J.S.J et al., "The Constant Domain of IgG Is a Possible Target Antigen for Immunotherapy of B Cell Malignancies in HLA-A1 Mismatched Transplantation," *Blood* 98:404a-405ad, The American Society of Hematology (Dec. 2001).

Gibbs, J. "Immobilization Principles—Selecting the Surface," in *ELJSA Technical Bulletin—No. 1*, Corning Incorporated, Acton, MA, pp. 1-8 (Jul. 2001).

Godkin, A.J. et al., "Naturally Processed HLA Class II Peptides Reveal Highly Conserved Immunogenic Flanking Region Sequence Preferences that Reflect Antigen Processing Rather Than Peptide-MHC Interactions," *J. Immunol.* 166:6720-6727, American Association of Immunologists (Jun. 2001).

Gorga, J.C. et al., "Purification and Characterization of Class II Histocompatibility Antigens from a Homozygous Human B Cell Line," *J. Biol. Chem.* 262:16087-16094, The American Society for Biochemistry and Molecular Biology (1987).

Greten, T.F., and Schneck, J.P., "Development and Use of Multimeric Major Histocompatibility Complex Molecules," *Clin. Diagn. Lab. Immunol.* 9:216-220, American Society for Microbiology (Mar. 2002).

Hansen, T.H. and Sachs, D.H., "Chapter 16: The Major Histocompatibility Complex," in *Fundamental Immunology 2nd Ed.*, Paul, W.E., ed., Raven Press Publishing, New York, NY, pp. 445-487 (1989).

Hermans, I.F. et al., "The Vital assay: a versatile fluorometric technique for assessing CTL- and NKT-mediated cytotoxicity against multiple targets in vitro and in vivo," *J. Immunol. Methods* 285:25-40, North-Holland Publishing Co. (Feb. 2004).

Henderson, R.A. et al., "Direct identification of an endogenous peptide recognized by multiple HLA-A2.1-specific cytotoxic T cells," *Proc. Natl. Acad. Sci. U.S.A.* 90:10275-10279, National Academy of Sciences (1993).

Hengel, H. et al., "Frequency of Herpes Simplex Virus-Specific Murine Cytotoxic T Lymphocyte Precursors in Mitogen- and Antigen-Driven Primary in vitro T Cell Responses," *J. Immunol.* 139:4196-4202, The American Association of Immunologists (1987).

Herr, W. et al., "Detection and quantification of blood-derived $CD8^+T$ lymphocytes secreting tumor necrosis factor α in response to HLA-A2. 1-binding melanoma and viral peptide antigens," *J. Immunol. Methods* 191:131-142, North-Holland Publishing Co. (1996).

Herr, W. et al., "The use of computer-assisted video image analysis for the quantification of $CD8^+T$ lymphocytes producing tumor necrosis factor α spots in response to peptide antigens," *J. Immunol. Methods* 203:141-152 North-Holland Publishing Co. (1997).

Hickling, J.K. et al., "Varicella-Zoster Virus-Specific Cytotoxic T Lymphocytes (Tc): Detection and Frequency Analysis of HLA Class I-Restricted Tc in Human Peripheral Blood," *J. Virol.* 61:3463-3469, American Society for Microbiology (1987).

Hörig, H. et al., "An in vitro study of the dynamic features of the major histocompatibility complex class I complex relevant to its role as a versatile peptide-receptive molecule," *Proc. Natl. Acad. Sci. U.S.A.* 94:13826-13831, National Academy of Sciences (1997).

Hugues, S. et al., "Generation and use of alternative multimers of peptide/MHC complexes," *J Immunol. Methods* 268:83-92, North-Holland Publishing Co. (Oct. 2002).

Hunkapiller, M.W. et al., "Isolation of Microgram Quantities of Proteins from Polyacrylamide Gels for Amino Acid Sequence Analysis," *Methods Enzymol.* 91:227-236, Academic Press (1983).

Hunt et al., "Characterization of Peptides Bound to the Class I MHC Molecule HLA-A2.1 by Mass Spectrometry," *Science* 255:1261-1263 (1992).

Jäger et al., "Impact of antigen presentation on TCR modulation and cytokine release: implications for detection and sorting of antigen-specific CD8+ T cells using HLA-A2 wild-type or HLA-A2 mutant tetrameric complexes," *J. Immunol.* 168(6):2766-2772 (Mar. 2002).

Jensen et al., "Europium Fluoroimmunoassay for Measuring Peptide Binding to MHC Class I Moldecules," *Journal of Immunological Methods* 215:71-80 (1998).

Kadival, G.V. et al., "Characterization of Serologic and Cell-Mediated Reactivity of a 38-kDa Antigen Isolated from *Mycobacterium tuberculosis*," *J. Immunol.* 139:2447-2451, The American Association of Immunologists (1987).

Kawakami, Y. et al., "Cloning of the gene coding for a shared human melanoma antigen recognized by autologous T cells infiltrating into tumor," *Proc. Natl. Acad. Sci. U.S.A.* 91:3515-3519, National Academy of Sciences (1994).

Kawakami, Y. et al., "Identification of the Immunodominant Peptides of the MART-I Human Melanoma Antigen Recognized by the Majority of HLA-A2-restricted Tumor Infiltrating Lymphocytes," *J. Exp. Med.* 180:347-352, Rockefeller University Press (1994).

Klein, J., and Sato, A., "The HLA System—Second of Two Parts," *N. Engl. J Med.* 343:782-786, Massachusetts Medical Society (Sep. 2000).

Kozono et al., "Production of Soluble MHC Class II Proteins with Covalently Bound Single Peptides," *Nature*, 369(6476):151-154(1994).

Kuhns, J.J. et al., "Poor Binding of a HER-2/neu Epitope (GP2) to HLA-A2.1 Is Due to a Lack of Interactions with the Center of the Peptide," *J. Biol. Chem.* 274:36422-36427, The American Society for Biochemistry and Molecular Biology (1999).

Lazar, E et al., "Transforming Growth Factor α Mutation of Aspartic Acid 47 and Leucine 48 Results in Different Biological Activities," *Mol. Cell Biol.* 8:1247-1252, American Society for Microbiology (1988).

Maeurer, M.J. et al., "Improved Detection of Melanoma Antigen-Specific T Cells Expressing Low or High Levels of CD8 by HLA-A2 Tetramers Presenting a Melan-A/Mart-1 Peptide Analogue," *Int. J. Cancer* 97:64-71, Wiley-Liss, Inc. (Jan. 2002).

Mallet-Designe, V.I. et al., "Detection of Low-Avidity $CD4^+T$ Cells Using Recombinant Artificial APC: Following the Antiovalbumin Immune Response," *J Immunol.* 170:123-131, American Association of Immunologists (Jan. 2003).

Marin et al., "Cloning and expression of a single-chain antibody fragment specific for a monomorphic determinant of class I molecules of the human major histocompatibility complex," *Hybridoma* 14(5):443-551 (Oct. 1995).

Marx, J.L., "Histocompatibility Restriction Explained," *Science* 235:843-844, American Association for the Advancement of Science (1987).

McMichael, A.J., and Kelleher, A., "The arrival of HLA class II tetramers," *J Clin. Invest.* 104:1669-1670, American Society for Clinical Investigation (1999).

Men, Y. et al., "Assessment of Immunogenicity of Human Melan-A Peptide Analogues in HLA-A $O201/K^b$ Transgenic Mice," *J Immunol.* 162:3566-3573, The American Association of Immunologists (1999).

Merriam-Webster OnLine dictionary, definition for the term "reconstitute," downloaded from www.m-w.com on Nov. 3, 2006.

Miller et al., "Rapid Determination of Class I Peptide Binding Motifs Using Codon-Based Random Peptide Phage Display Libraries," *Journal of Cellular Biochemistry* (Supplement), 18D:292 (1994).

Nepom, CT. et al., "HLA Class II Tetramers—Tools for Direct Analysis of Antigen-Specific CD4+ T Cells," *Arthritis Rheum.* 46:5-12, Wiley-Liss, Inc. (Jan. 2002).

Ogg, G.S., and McMichael, A.J., "HLA-peptide tetrameric complexes," *Curr. Opin. Immunol.* 10:393-396, Current Biology (1998).

(56) References Cited

OTHER PUBLICATIONS

Passmore et al. "Preparative-Scale Purification and Characterization of MHC Class II Monomers," *Journal of Immunological Methods* 155(2):193-200 (1992).

Plytycz and Seljelid, "MFIC Molecules and Lymphocytes: Evolutionary Perspective," *Archivum Immunologiae et Therapiae Experimentalis* 46:137-142 (1998).

Qiagen, product information sheet for Ni-NTA agarose, retrieved from www1.qiagen.com on Jan. 23, 2009.

Reichstetter, S. et al., "Distinct T Cell Interactions with HLA Class II Tetramers Characterize a Spectrum of TCR Affinities in the Human Antigen-Specific T Cell Response," *J. Immunol.* 165:6994-6998, The American Association of Immunologists (Dec. 2000).

Robert, B. et al., "Antibody-conjugated MHC class I tetramers can target tumor cells for specific lysis by T lymphocytes," *Eur. J. Immunol.* 30:3165-3170, VCH Verlagsgesellschaft (2000).

Robinson, M.A., and Kindt, T.J., "Chapter 17: Major Histocompatibility Complex Antigens and Genes," in *Fundamental Immunology 2nd Ed.*, Paul, W.E., ed., Raven Press Ltd., New York, NY, pp. 489-539 (1989).

Rötzschke, O. et al., "Conformational variants of class II MHC/peptide complexes induced by N- and C-terminal extensions of minimal peptide epitopes," *Proc. Natl.. Acad. Sci USA* 96:7445-7450, National Academy of Sciences (1999).

Ruppert, J. et al., "Prominent Role of Secondary Anchor Residues in Peptide Binding to HLA-A2.1 Molecules," *Cell* 74:929-937, Cell Press (1993).

Sadegh-Nasseri et al., "A kinetic intermediate in the reaction of an antigenic peptide and I-$E^k$," *Nature* 337(6204):274-276 (Jan. 1989).

Samelson, L.E et al., "T Cell Antigen Receptor Phosphorylation Induced by an Anti-Receptor Antibody," *J. Immunol.* 139:2708-2714, The American Association of Immunologists (1987).

Sette, A. et al., "Structural characteristics of an antigen required for its interaction with Ia and recognition by T cells," *Nature* 328:395-399, Nature Publishing Group (1987).

Seffernick et al., *J. Bacteriology*, vol. 183, pp. 2405-2410 (2001).

Shmanai, V.V. et al., "Oriented antibody immobilization to polystyrene macrocarriers for immunoassay modified with hydrazide derivatives of poly(meth)acrylic acid," *BMC Biotechnol.* 1:4, 5 pages, BioMed Central (Aug. 2001).

Sliz, P. et al., "Crystal Structures of Two Closely Related but Antigenically Distinct HLA-A2/Melanocyte-Melanoma Tumor-Antigen Peptide Complexes," *J. Immunol.* 167:3276-3284, The American Association of Immunologists (Sep. 2001).

Smith, J.D. et al., "Extensive peptide ligand exchange by surface class I major histocompatibility complex molecules independent of exogenous $\beta_2$-microglobulin," *Proc. Natl. Acad. Sci. U.S.A.* 89:7767-7771, National Academy of Sciences (1992).

Sørensen, A.L. et al., "Purification and Characterization of a Low-Molecular-Mass T-Cell Antigen Secreted by *Mycobacterium tuberculosis*," *Infect. Immun.* 63:1710-1717, American Society for Microbiology (1995).

Springfrog, "Temperature Converter," accessed online at http://springfrog.com/converter/temperature.htm, 2 pages (accessed 2008).

Stone, J.D. et al., "T-Cell Activation by Soluble MHC Oligomers Can Be Described by a Two-Parameter Binding Model," *Biophys. J.* 81:2547-2557, Biophysical Society (Nov. 2001).

Sugita et al., "Assembly and retention of CD1b heavy chains in the endoplasmic reticulum," *J. Immunol.* 159(5):2358-2365 (Sep. 1997).

Sylvester-Hvid et al., "Establishment of a quantitative ELISA capable of determining peptide—HMC class I interaction," Tissue Antigens, 59(4):251-258 (Apr. 2002).

Tao, M.H., and Morrison, S.L. et al., "Studies of Aglycosylated Chimeric Mouse-Human IgG. Role of Carbohydrate in the Structure and Effector Functions Mediated by the Human IgG Constant Region," *J. Immunol.* 143:2595-2601, The American Association of Immunologists (1989).

Thorley-Lawson, D.A., and Israelsohn, E.S., "Generation of specific cytotoxic T cells with a fragment of the Epstein-Barr virus-encoded p63/latent membrane protein," *Proc. Natl. Acad. Sci. U.S.A.* 84:5384-5388, National Academy of Sciences (1987).

Tissot et al., "Characterizing the functionality of recombinant T-cell receptors in vitro: a pMHC tetramer based approach," *J. Immunol. Methods* 236(I-2):147-165 (Mar. 2000).

Tompkins et al., "A Europium Fluoroimmunoassay for Measuring Binding of Antigen to Class H MHC Glycoproteins," *Journal of Immunological Methods*, 163:209-216 (1993).

Tsien, R.Y. et al., "T-cell mitogens cause early changes in cytoplasmic free $Ca^{2+}$ and membrane potential in lymphocytes," *Nature* 295:68-71, Nature Publishing Group (1982).

Tsomides, T.J. et al., "An optimal viral peptide recognized by $CD8^+$ T cells binds very tightly to the restricting class I major histocompatibility complex protein on intact cells but not to the purified class I protein," *Proc. Natl.. Acad. Sci. U.S.A.* 88:11276-11280, National Academy of Sciences (1991).

Turner, M.J. et al., "Purification of Papain-solubilized Histocompatibility Antigens from a Cultured Human Lymphoblastoid Line, RPMI 4265," *J. Biol. Chem.* 250:4512-4519, American Society for Biochemistry and Molecular Biology (1975).

Ulbrecht et al., "Interaction of HLA-E with Peptides and the Peptide Transporter In Vitro: Implications for its Function in Antigen Presentation," *The Journal of Immunology* 160: 4375-4385 (1998).

Valmori, D. et al., "Diversity of the Fine Specificity Displayed by HLA-A 0201-Restricted CTL Specific for the Immunodominant Melan-A/MART-1 Antigenic Peptide," *J Immunol.* 161:6956-6962, The American Association of Immunologists(1998).

Van Der Burg, S.H. et al., "An HLA Class I Peptide-Binding Assay Based on Competition for Binding to Class I Molecules on Intact Human B Cells. Identification of Conserved HIV-1 Polymerase Peptides Binding to HLA-A 0301," *Hum. Immunol.* 44:189-198, Elsevier/North-Holland (1995).

Van Der Burg, S.H., et al., "Immunogenicity of Peptides Bound to MHC Class I Molecules Depends on the MHC-Peptide Complex Stability," *J. Immunol.* 156:3308-3314, The American Association of Immunologists (1996).

Veilleux, J.K. and Duran, L.W., "Covalent immobilization of biomolecules, to preactivated surfaces, " available online at www.devicelink.com/ivdt/archive/96/03/005.html, 6 pages (1996).

Wells, *Biochemistry*, 29: 8509-8517 (1990).

Welsh, R.M., "Assessing CD8 T Cell Number and Dysfunction in the Presence of Antigen," *J. Exp. Med.* 193:F19-F22, The Rockefeller University Press (Mar. 2001).

Wiuff, C. et al., "Evaluation of a novel enzyme-linked immunosorbent assay for detection of antibodies against *Salmonella*, employing a stable coating of lipopolysaccharide-derived antigens covalently attached to polystyrene microwells," *J. Vet. Diagn. Invest.* 12:130-135, American Association of Veterinary Laboratory Diagnosticians (2000).

Woll, M.M. et al., "Direct Measurement of Peptide-Specific CD8+ T cells Using HLA-A2:Ig Dimer for Monitoring the in Vivo Immune Response to a HER2/neu Vaccine in Breast and Prostate Cancer Patients," *J. Clin. Immunol.* 24:449-461, Kluwer Academic/Plenum Publishers (Jul. 2004).

Zarutskje, J.A. et al., "A Conformational Change in the Human Major Histocompatibility Complex Protein HLA-DR1 Induced by Peptide Binding," *Biochemistry* 38:5878-5887, American Chemical Society (1999).

* cited by examiner

METHODS AND SYSTEMS FOR DETECTING MHC CLASS I BINDING PEPTIDES

CROSS REFERENCE TO RELATED APPLICATION

This application is a Continuation of U.S. patent application Ser. No. 10/269,473 filed on Oct. 11, 2002, now abandoned.

FIELD OF THE INVENTION

This invention relates generally to the field of immunoassays, especially using immunoassays to detect and measure binding of peptides to MHC alleles.

BACKGROUND OF THE INVENTION

The Class I histocompatibility ternary complex consists of three parts associated by noncovalent bonds. A transmembrane protein, called the MHC heavy chain is mostly exposed at the cell surface. The cell surface domains of the MHC heavy chain contain two segments of alpha helix that form two ridges with a groove between them. A short peptide binds noncovalently ("fits") into this groove between the two alpha helices, and a molecule of beta-2 microglobulin binds noncovalently along side the outer two domains of the MHC monomer, forming a ternary complex. Peptides that bind noncovalently to one MHC subtype heavy chain usually will not bind to another subtype. However, all bind with the same type of beta-2 microglobulin. MHC molecules are synthesized and displayed by most of the cells of the body.

In humans, MHC molecules are referred to as HLA molecules. Humans primarily synthesize three different subtypes of MHC class 1 molecules designated HLA-A, HLA-B and HLA-C, differing only in the heavy chains.

The MHC works coordinately with a specialized type of T cell (the cytotoxic T cell) to rid the body of "nonself" or foreign viral proteins. The antigen receptor on T-cells recognizes an epitope that is a mosaic of the bound peptide and portions of the alpha helices of the making up the groove flanking it. Following generation of peptide fragments by cleavage of a foreign protein, the presentation of peptide fragments by the MHC molecule allows for MHC-restricted cytotoxic T cells to survey cells for the expression of "nonself" or foreign viral proteins. A functional T-cell will exhibit a cytotoxic immune response upon recognition of an MHC molecule containing bound antigenic peptide for which the T-cell is specific.

In the performance of these functions in humans, HLA-A, B, and C heavy chains interact with a multitude of peptides of about 8 to about 10, possibly about 8 to about 11, or about 8 to about 12 amino acids in length. Only certain peptides bind into the binding pocket in the heavy chain of each HLA sub-type as the monomer folds, although certain subtypes cross-react. By 1995, complete coding region sequences had been determined for each of 43 HLA-A, 89 HLA-B and 11 HLA-C alleles (P. Parham et al., *Immunology Review* 143: 141-180, 1995).

Class II histocompatibility molecules consist of two transmembrane polypeptides that interact to form a groove at their outer end which, like the groove in class I molecules, noncovalently associates with an antigenic peptide. However, the antigenic peptides bound to class II molecules are derived from antigens that the cell has taken in from its surroundings. In addition, peptides that hind to class II histocompatibility molecules are 15 to about 25 or to about 30 amino acids in length. Only cells, such as macrophages, dendritic cells and B lymphocytes, that specialize in taking up antigen from extracellular fluids, express class II molecules.

It has long been thought that discovery of which antigen fragments will be recognized by class I MHC-restricted T-cells can lead to development of effective vaccines against cancer and viral infections. A number of approaches have been developed wherein algorithms are used to predict the amino acid sequence of HLA A, B, or C-binding peptides and several are available on the internet. For example, U.S. Pat. No. 6,037,135 describes a matrix-based algorithm that ranks peptides for likelihood of binding to any given HLA-A allele. Similarly, most prediction methods are limited to a set of alleles. Consequently, the predicted peptides may not bind to MHC monomers from a whole population of patients and thus may not be globally effective.

Another approach to identifying MHC-binding peptides uses a competition-based binding assay. All competition assays yield a comparison of binding affinities of different peptides. However, such assays do not yield an absolute dissociation constant since the result is dependent on the reference peptide used.

Still another approach used for determining MHC-binding peptides is the classical reconstitution assay, e.g. using "T2" cells, in which cells expressing an appropriate MHC allele are "stripped" of a native binding peptide by incubating at pH 2-3 for a short period of time. Then, to determine the binding affinity of a putative MHC-binding peptide for the same MHC allele, the stripped MHC monomer is combined in solution with the putative MHC-binding peptide, beta2-microglobulin and a conformation-dependent monoclonal antibody. The difference in fluorescence intensity determined between cells incubated with and without the test binding peptide after labeling, for example, either directly with the labeled monoclonal antibody or a fluorescence-labeled secondary antibody, can be used to determine binding of the test peptide. However, soluble MHC monomers stripped at low pH aggregate immediately, making their use in high through-put assays difficult and impractical.

There are currently a series of in vitro assays for cell mediated immunity which use cells from the donor. The assays include situations where the cells are from the donor, however, many assays provide a source of antigen presenting cells from other sources, e.g., B cell lines. These in vitro assays include the cytotoxic T lymphocyte assay; lymphoproliferative assays, e.g., tritiated thymidine incorporation; the protein kinase assays, the ion transport assay and the lymphocyte migration inhibition function assay (Hickling, J. K. et al, J. Virol., 61: 3463 (1987); Hengel, H. et al, J. Immunol., 139: 4196 (1987); Thorley-Lawson, D. A. et al, Proc. Natl. Acad. Sci. USA, 84: 5384 (1987); Kadival, G. J. et al, J. Immunol., 139: 2447 (1987); Samuelson, L. E. et el, J. Immunol., 139: 2708 (1987); Cason, J. et al, J. Immunol. Meth., 102: 109 (1987); and Tsein, R. J. et al, Nature, 293: 68 (1982)). These assays are disadvantageous in that they may lack true specificity for cell mediated immunity activity, they require antigen processing and presentation by an APC of the same MHC type, they are slow (sometimes lasting several days), and some are subjective and/or require the use of radioisotopes.

Yet another approach to identifying MHC class I-binding peptides utilizes formation of MHC tetramers, which are complexes of four MHC monomers with streptavidin, a molecule having tetrameric binding sites for biotin, to which is bound a fluorochrome, e.g., phycoerythrin. For class I monomers, soluble subunits of β2-microglobulin, the peptide fragment containing a putative T-cell epitope, and of a MHC heavy chain corresponding to the predicted MHC subtype of the peptide fragment of interest, are obtained by expression of the polypeptides in host cells. Each of the four monomers contained in the MHC tetramer is produced as a monomer by refolding these soluble subunits under conditions that favor assembly of the soluble units into reconstituted monomers, each containing a beta2-microglobulin, a peptide fragment, and the corresponding MHC heavy chain. An MHC tetramer is constructed from the monomers by biotinylation of the monomers and subsequent contact of the biotinylated reconstituted monomers with fluorochrome-labeled streptavidin. When contacted with a diverse population of T cells, such as is contained in a sample of the peripheral blood lymphocytes (PBLs) of a subject, those tetramers containing reconstituted monomers that are recognized by a T cell in the sample will bind to the matched T cell. Contents of the reaction is analyzed using fluorescence flow cytometry, to determine, quantify and/or isolate those T-cells having a MHC tetramer bound thereto (See U.S. Pat. No. 5,635,363).

At least one other test is required to determine whether a test peptide recognized by a T-cell by the MHC tetramer assay will activate the T-cell to generate an immune response, a so-called "functional test". The enzyme-linked immunospot (ELISpot) assay has been adapted for the detection of individual cells secreting specific cytokines or other effector molecules by attachment of a monoclonal antibody specific for a cytokine or effector molecule on a microplate. Cells stimulated by an antigen are contacted with the immobilized antibody. After washing away cells and any unbound substances, a tagged polyclonalantibody or more often, a monoclonal antibody, specific for the same cytokine or other effector molecule is added to the wells. Following a wash, a colorant that binds to the tagged antibody is added such that a blue-black colored precipitate (or spot) forms at the sites of cytokine localization. The spots can be counted manually or with automated ELISpot reader system to quantitated the response. A final confirmation of T-cell activation by the test peptide may require in vivo testing, for example in a mouse model. Thus, the route to final confirmation of the efficacy of a MHC-binding peptide is expensive and time consuming.

Thus, there is still a need in the art for new and better systems and methods for preliminary screening assays identifying putative MHC class I-binding peptides and for measuring peptide binding to MHC class I alleles, such as HLA-A, B or C, especially an in vitro assay in solid phase format. There is also a need in the art to develop methods to determine the MHC-binding affinity of MHC-binding peptides and for a measurement for the dissociation rate of a bound peptide from the MHC molecule.

SUMMARY OF THE INVENTION

The present invention is based on the discovery that MHC class I monomers when immobilized to a solid surface are still capable of reconstituting to incorporate from solution an MHC-binding peptide and form a ternary complex.

Accordingly, in one embodiment the invention provides a system comprising a solid surface, wherein the surface has attached thereto one or more MHC monomer or modified MHC monomer, wherein the monomer denatures in a denaturing condition and reconstitutes to form a ternary complex containing a suitable MHC-binding peptide in the binding pocket under reconstituting conditions. In another embodiment a kit comprising the invention system is also provided.

In yet another embodiment, the invention provides methods for determining binding between a MHC monomer or modified MHC monomer and a putative MHC-binding peptide therefor. In this method for assaying binding of a putative MHC-binding peptide, a solid surface having attached thereto a plurality of previously denatured MHC monomers or modified MHC monomers is incubated under reconstituting conditions in the presence and absence of the putative MHC-binding peptide such that the monomers reconstitute to form a ternary complex containing a suitable MHC-binding peptide under the reconstituting conditions. Binding to the ternary complex of a monoclonal antibody that does not bind to dissociated components of the complex indicates binding between the putative MHC-binding peptide and the monomers.

In still another embodiment, the invention provides methods for determining the degree of binding affinity of an MHC monomer or modified MHC monomer for a putative MHC-binding peptide therefor. In this embodiment, at least one denatured MHC monomer or modified MHC monomer attached to a solid surface is incubated under reconstituting conditions with the putative MHC-binding peptide and a monoclonal antibody that specifically binds to a conformational epitope of a corresponding reconstituted MHC monomer that is not present in the denatured monomer. Binding of the monoclonal antibody to a monomer that binds to the putative MHC-binding peptide is compared with binding of the monoclonal antibody to a corresponding monomer having a known MHC-binding peptide bound thereto. The difference in the binding indicates the relative degree of binding affinity of the reconstituted monomer for the putative MHC-binding peptide.

In still another embodiment, the invention provides methods for determining the stability at 37° C. of an MHC monomer or modified MHC monomer for a putative MHC-binding peptide therefor. In this embodiment, at least one denatured MHC monomer or modified MHC monomer attached to a solid surface is incubated under reconstituting conditions with the putative MHC-binding peptide and a monoclonal antibody that specifically binds to a conformational epitope of a corresponding reconstituted MHC monomer that is not present in the denatured monomer. After the reconstituted ternary complex with the monoclonal antibody is incubated at different temperatures and different times. The difference in the signal obtained at different temperatures and different times, indicates the relative stability of the reconstituted monomer for the putative MHC-binding peptide.

BRIEF DESCRIPTION OF THE FIGURES

FIG. 7A shows the results with HLA-A*0201/Mart1

2635L (Linear regression equation: y=1555.5x+39.787; R2=0.9889. FIG. 7B shows the results with HLA heavy chain monomer HLA-A*0201/HIVpol (Linear regression equation: y=1487.1X+13.927, R2=0.9982)

DETAILED DESCRIPTION OF THE INVENTION

The present invention relates in general to immunoassays directed to detection and measurement of the binding affinity of MHC heavy chain monomers, especially MHC heavy chain monomers immobilized on a surface, for putative MHC-binding peptides. It is the discovery of the present invention that MHC heavy chain monomers and modified MHC monomers immobilized to a solid surface are still capable of refolding so as to bind from solution beta2-microglobulin and a MHC-binding peptide that has the requisite binding. Moreover, it is the discovery of the present invention that such binding can be detected in an immunoassay format, such as one utilizing a conformation-dependent monoclonal antibody that specifically binds to a ternary complex containing such refolded or reconstituted MHC monomers but does not bind to dissociated components of the ternary complex.

As used herein, the terms "MHC monomer" and "HLA monomer" refer to a class I MHC heavy chain that maintains the ability to assemble into a ternary complex with an appropriate MHC-binding or HLA-binding peptide and beta-2 microglobulin under renaturing conditions. The terms "MHC monomer" and HLA monomer" are also used to refer to the denatured form of the monomer that results from subjecting the ternary complex to denaturing conditions, causing the monomer to unfold and dissociate from a MHC-binding peptide and from beta-2 microglobulin.

Figure 9:
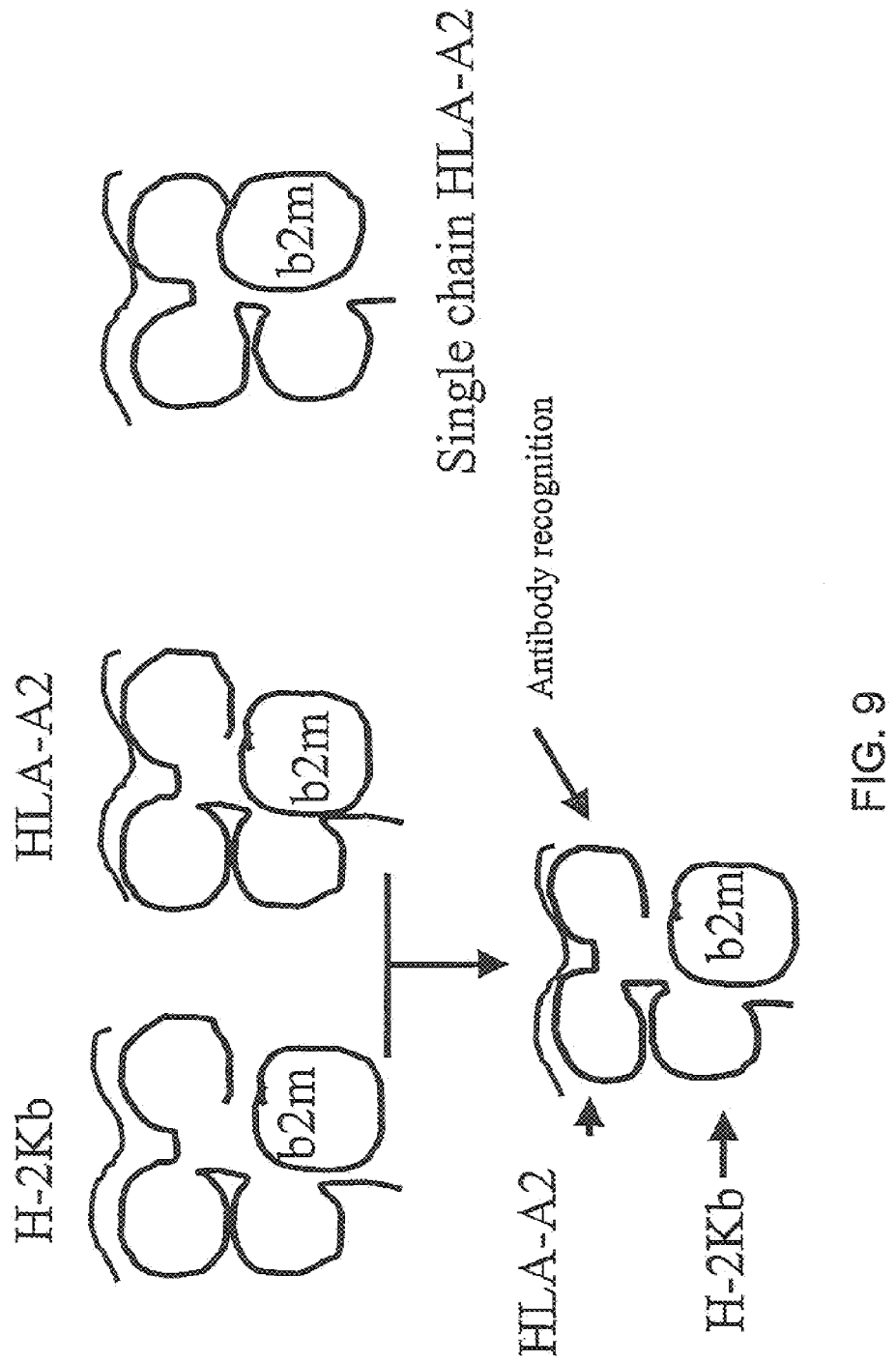
FIG. 9 is a schematic drawing showing formation of a human-mouse chimeric MHC modified monomer according to the invention.

As used herein, the terms "modified MHC monomer" and "modified HLA monomer" refer to class I monomers as described above, but which have been engineered to introduce modifications as described below. These terms also encompass functional fragments of the MHC monomer that maintain the ability to assemble into a ternary complex with an appropriate MHC-binding or HLA-binding peptide and beta-2 microglobulin under renaturing conditions and to dissociate under denaturing conditions. For example, a functional fragment can comprise only the $\alpha_1$, $\alpha_2$, $\alpha_3$, domains, or only $\alpha_1$, $\alpha_2$ domains, of the class I heavy chain, i.e., the cell surface domains, that participate in formation of the ternary complex. In another embodiment, modified MHC monomers can be class I heavy chain molecules, or functional fragments thereof, contained in a fusion protein or "single chain" molecule and may further include an amino acid sequence functioning as a linker between cell surface domains of the monomer, a detectable marker or as a ligand to attach the molecule to a solid support that is coated with a second ligand with which the ligand in the fusion protein reacts. Moreover the terms "modified MHC monomer" and "modified HLA monomer" are intended to encompass chimera containing domains of class I heavy chain molecules from more than one species or from more than one class I subclass. FIG. 9 herein illustrates preparation of a chimera by substitution of a mouse H-2 Kb domain for one of the three alpha domains in a human HLA-A2 fragment. Such a molecule is conveniently expressed as a single chain with optional amino acid linkers between subunits or as a fusion protein as is known in the art.

Preparation of Monomers

The Class I MHC in humans is located on chromosome 6 and has three loci, HLA-, HLA-B, and HLA-C. The first two loci have a large number of alleles encoding alloantigens. These are found to consist of a 44 Kd heavy chain subunit and a 12 Kd.beta$_2$-microglobulin subunit which is common to all antigenic specificities. For example, soluble HLA-A2 can be purified after papain digestion of plasma membranes from the homozygous human lymphoblastoid cell line J-Y as described by Turner, M. J. et al., J. Biol. Chem. (1977) 252: 7555-7567. Papain cleaves the 44 Kd heavy chain close to the transmembrane region, yielding a molecule comprised of $\alpha_1$, $\alpha_2$, $\alpha_3$ domains and beta-2 microglobulin.

The MHC monomers can be isolated from appropriate cells or can be recombinantly produced, for example as described by Paul et al, Fundamental Immunology, 2d Ed., W. E. Paul, ed., Ravens Press N.Y. 1989, Chapters 16-18) and readily modified, as described below.

The term "isolated" as applied to MHC monomers herein refers to an MHC glycoprotein heavy chain of MHC class I, which is in other than its native state, for example, not associated with the cell membrane of a cell that normally expresses MHC. This term embraces a full length subunit chain, as well as a functional fragment of the MHC monomer. A functional fragment is one comprising an antigen binding site and sequences necessary for recognition by the appropriate T cell receptor. It typically comprises at least about 60-80%, typically 90-95% of the sequence of the full-length chain. As described herein, the "isolated" MHC subunit component may be recombinantly produced or solubilized from the appropriate cell source.

It is well known that native forms of "mature" MHC glycoprotein monomers will vary somewhat in length because of deletions, substitutions, and insertions or additions of one or more amino acids in the sequences. Thus, MHC monomers are subject to substantial natural modification, yet are still capable of retaining their functions. Modified protein chains can also be readily designed and manufactured utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

In general, modifications of the genes encoding the MHC monomer may be readily accomplished by a variety of well-known techniques, such as site-directed mutagenesis. The effect of any particular modification can be evaluated by routine screening in a suitable assay for the desired characteristic. For instance, a change in the immunological character of the subunit can be detected by competitive immunoassay with an appropriate antibody. The effect of a modification on the ability of the monomer to activate T cells can be tested using standard in vitro cellular assays or the methods described in the example section, below. Modifications of other properties such as redox or thermal stability, hydrophobicity, susceptibility to proteolysis, or the tendency to aggregate are all assayed according to standard techniques.

This invention provides amino acid sequence modification of MHC monomers prepared with various objectives in mind, including increasing the affinity of the subunit for antigenic peptides and/or T cell receptors, facilitating the stability, purification and preparation of the subunits. The monomers may also be modified to modify plasma half life, improve therapeutic efficacy, or to lessen the severity or occurrence of side effects during therapeutic use of complexes of the present invention. The amino acid sequence modifications of the subunits are usually predetermined variants not found in nature or naturally occurring alleles. The variants typically exhibit the same biological activity (for example, MHC-peptide binding) as the naturally occurring analogue.

Insertional modifications of the present invention are those in which one or more amino acid residues are introduced into a predetermined site in the MHC monomer and which displace the preexisting residues. For instance, insertional modifications can be fusions of heterologous proteins or polypeptides to the amino or carboxyl terminus of the subunits.

Other modifications, include fusions of the monomer with a heterologous signal sequence and fusions of the monomer to polypeptides having enhanced plasma half life (ordinarily>about 20 hours) such as immunoglobulin chains or fragments thereof as is known in the art.

Substitutional modifications are those in which at least one residue has been removed and a different residue inserted in its place. Nonnatural amino acid (i.e., amino acids not normally found in native proteins), as well as isosteric analogs (amino acid or otherwise) are also suitable for use in this invention.

Substantial changes in function or immunological identity are made by selecting substituting residues that differ in their effect on maintaining the structure of the polypeqptide backbone (e.g., as a sheet or helical conformation), the charge or hydrophobicity of the molecule at the target site, or the bulk of the side chain. The substitutions which in general are expected to produce the greatest changes in function will be those in which (a) a hydrophilic residue, e.g., serine or threonine, is substituted for (or by) a hydrophobic residue, e.g. leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamine or aspartine; or (d) a residue having a bulky side chain, e.g., phenylalanine, is substituted for (or by) one not having a side chain, e.g., glycine.

Substitutional modifications of the monomers also include those where functionally homologous (having at least about 70% homology) domains of other proteins are substituted by routine methods for one or more of the MHC subunit domains. Particularly preferred proteins for this purpose are domains from other species, such as murine species as illustrated in FIG. 9 herein.

Another class of modifications are deletional modifications. Deletions are characterized by the removal of one or more amino acid residues from the MHC monomer sequence. Typically, the transmembrane and cytoplasmic domains are deleted. Deletions of cysteine or other labile residues also may be desirable, for example in increasing the oxidative stability of the MHC complex. Deletion or substitutions of potential proteolysis sites, e.g., ArgArg, is accomplished by deleting one of the basic residues or substituting one by glutaminyl or histidyl residues.

A preferred class of substitutional or deletional modifications comprises those involving the transmembrane region of the subunit. Transmembrane regions of MHC monomers are highly hydrophobic or lipophilic domains that are the proper size to span the lipid bilayer of the cellular membrane. They are believed to anchor the MHC molecule in the cell membrane. Inactivation of the transmembrane domain, typically by deletion or substitution of transmembrane domain hydroxylation residues, will facilitate recovery and formulation by reducing its cellular or membrane lipid affinity and improving its aqueous solubility. Alternatively, the transmembrane and cytoplasmic domains can be deleted to avoid the introduction of potentially immunogenic epitopes. Inactivation of the membrane binding function is accomplished by deletion of sufficient residues to produce a substantially hydrophilic hydropathy profile at this site or by substitution with heterologous residues which accomplish the same result.

A principal advantage of the transmembrane-inactivated MHC monomer is that it may be secreted into the culture medium of recombinant hosts. This variant is soluble in body fluids such as blood and does not have an appreciable affinity for cell membrane lipids, thus considerably simplifying its recovery from recombinant cell culture. Typically, modified MHC monomers of this invention will not have a functional transmembrane domain and preferably will not have a functional cytoplasmic sequence. Such modified MHC monomers will consist essentially of the effective portion of the extracellular domain of the MHC monomer. In some circumstances, the monomer comprises sequences from the transmembrane region (up to about 10 amino acids), so long as solubility is not significantly affected.

For example, the transmembrane domain may be substituted by any amino acid sequence, e.g., a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) monomer, these monomers are secreted into the culture medium of recombinant hosts.

Glycosylation variants are included within the scope of this invention. They include variants completely lacking in glycosylation (unglycosylated) and variants having at least one less glycosylated site than the native form (deglycosylated) as well as variants in which the glycosylation has been changed. Included are deglycosylated and unglycosylated amino acid sequence variants, deglycosylated and unglycosylated subunits having the native, unmodified amino acid sequence. For example, substitutional or deletional mutagenesis is employed to eliminate the N- or O-linked glycosylation sites of the subunit, e.g., the asparagine residue is deleted or substituted for by another basic residue such as lysine or histidine. Alternatively, flanking residues making up the glycosylation site are substituted or deleted, even though the asparagine residues remain unchanged, in order to prevent glycosylation by eliminating the glycosylation recognition site. Additionally, unglycosylated MHC monomers which have the amino acid sequence of the native monomers are produced in recombinant prokaryotic cell culture because prokaryotes are incapable of introducing glycosylation into polypeptides.

Glycosylation variants are conveniently produced by selecting appropriate host cells or by in vitro methods. Yeast, for example, introduce glycosylation which varies significantly from that of mammalian systems. Similarly, mammalian cells having a different species (e.g., hamster, murine, insect, porcine, bovine or ovine) or tissue origin (e.g., lung, liver, lymphoid, mesenchymal or epidermal) than the MHC source are routinely screened for the ability to introduce variant glycosylation as characterized for example by elevated levels of mannose or variant ratios of mannose, fucose, sialic acid, and other sugars typically found in mammalian glycoproteins. In vitro processing of the subunit typically is accomplished by enzymatic hydrolysis, e.g., neuraminidase digestion.

MHC glycoproteins suitable for use in the present invention have been isolated from a multiplicity of cells using a variety of techniques including solubilization by treatment with papain, by treatment with 3M KCl, and by treatment with detergent. For example, detergent extraction of Class I protein followed by affinity purification can be used. Detergent can then be removed by dialysis or selective binding beads. The molecules can be obtained by isolation from any MHC I bearing cell, for example from an individual suffering from a targeted cancer or viral disease.

Isolation of individual heavy chain from the isolated MHC glycoproteins is easily achieved using standard techniques known to those skilled in the art. For example, the heavy chain can be separated using SDS/PAGE and electroelution of the heavy chain from the gel (see, e.g., Dornmair et al., supra and Hunkapiller, et al., Methods in Enzymol. 91:227-236 (1983). Separate subunits from MHC 1 molecules are also isolated using SDS/PAGE followed by electroelution as described in Gorga et al. J. Biol. Chem. 262:16087-16094 (1987) and Dornmair et al. Cold Spring Harbor Symp. Quant. Biol. 54:409-416 (1989) Those of skill will recognize that a number of other standard methods of separating molecules can be used, such as ion exchange chromatography, size exclusion chromatography or affinity chromatography.

Alternatively, the amino acid sequences of a number of Class I proteins are known, and the genes have been cloned, therefore, the heavy chain monomers can be expressed using recombinant methods. These techniques allow a number of modifications of the MHC monomers as described above. For instance, recombinant techniques provide methods for carboxy terminal truncation which deletes the hydrophobic transmembrane domain. The carboxy termini can also be arbitrarily chosen to facilitate the conjugation of ligands or labels, for example, by introducing cysteine and/or lysine residues into the molecule. The synthetic gene will typically include restriction sites to aid insertion into expression vectors and manipulation of the gene sequence. The genes encoding the appropriate monomers are then inserted into expression vectors, expressed in an appropriate host, such as $E.\ coli$, yeast, insect, or other suitable cells, and the recombinant proteins are obtained.

As the availability of the gene permits ready manipulation of the sequence, a second generation of construction includes chimeric constructs, as illustrated in FIG. 9. The $\alpha_1$, $\alpha_2$, $\alpha_3$, domains of the class I heavy chain are linked typically by the $\alpha_3$ domain of Class I with beta-2 microglobulin and coexpressed to stabilize the complex. The transmembrane and intracellular domains of the Class I gene can optionally also be included.

Construction of expression vectors and recombinant production from the appropriate DNA sequences are performed by methods known in the art. Standard techniques are used for DNA and RNA isolation, amplification, and cloning. Generally enzymatic reactions involving DNA ligase, DNA polymerase, restriction endonucleases, and the like, are performed according to the manufacturer's specifications. These techniques and various other techniques are generally performed according to Sambrook et al., Molecular Cloning—A Laboratory Manual, Cold Spring Harbor Laboratory, Cold Spring Harbor, N.Y., 1989. The procedures therein are believed to be well known in the art.

Expression can be in procaryotic or eucaryotic systems. Suitable eucaryotic systems include yeast, plant and insect systems, such as the $Drosophila$ expression vectors under an inducible promoter. Procaryotes most frequently are represented by various strains of $E.\ coli$. However, other microbial strains may also be used, such as bacilli, for example $Bacillus\ subtilis$, various species of $Pseudomonas$, or other bacterial strains. In such procaryotic systems, plasmid vectors which contain replication sites and control sequences derived from a species compatible with the host are used. For example, $E.\ coli$ is typically transformed using derivatives of pBR322, a plasmid derived from an $E.\ coli$ species by Bolivar et al., Gene (1977) 2:95. Commonly used procaryotic control sequences, which are defined herein to include promoters for transcription initiation, optionally with an operator, along with ribosome binding site sequences, including such commonly used promoters as the β-lactamase(penicillinase) and lactose (lac) promoter systems (Change et al., Nature (1977) 198:1056) and the tryptophan (trp) promoter system (Goeddel et al., Nucleic Acids Res. (1980) 8:4057) and the lambda-derived $P_L$ promoter and N-gene ribosome binding site (Shimatake et al., Nature (1981) 292:128). Any available promoter system compatible with procaryotes can be used.

The expression systems useful in the eucaryotic hosts comprise promoters derived from appropriate eucaryotic genes. A class of promoters useful in yeast, for example, include promoters for synthesis of glycolytic enzymes, including those for 3-phosphoglycerate kinase (Hitzeman, et al., J. Biol. Chem. (1980) 255:2073). Other promoters include, for example, those from the enolase gene (Holland, M. J., et al. J. Biol. Chem. (1981) 256:1385) or the Leu2 gene obtained from YEp13 (Broach, J., et al., Gene (1978) 8:121). A $Drosophila$ expression system under an inducible promoter (Invitrogen, San Diego, Calif.) can also be used.

Suitable mammalian promoters include the early and late promoters from SV40 (Fiers, et al., Nature (1978) 273:113) or other viral promoters such as those derived from polyoma, adenovirus II, bovine papilloma virus or avian sarcoma viruses. Suitable viral and mammalian enhancers are cited above.

The expression system is constructed from the foregoing control elements operably linked to the MHC sequences using standard methods, employing standard ligation and restriction techniques which are well understood in the art. Isolated plasmids, DNA sequences, or synthesized oligonucleotides are cleaved, tailored, and religated in the form desired.

Site-specific DNA cleavage is performed by treatment with the suitable restriction enzyme (or enzymes) under conditions which are generally understood in the art, and the particulars of which are specified by the manufacturer of these commercially available restriction enzymes. In general, about 1 μg of plasmid or DNA sequence is cleaved by one unit of enzyme in about 20 μl of buffer solution; an excess of restriction enzyme may be used to insure complete digestion of the DNA substrate. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed.

Restriction cleaved fragments may be blunt ended by treating with the large fragment of $E.\ coli$ DNA polymerase I (Klenow) in the presence of the four deoxynucleotide triphosphates (dNTPs) After treatment with Klenow, the mixture is extracted with phenol/chloroform and ethanol precipitated followed by running over a Sephadex G-50 spin column.

Synthetic oligonucleotides are prepared using commercially available automated oligonucleotide synthesizers. In the proteins of the invention, however, a synthetic gene is conveniently employed. The gene design can include restriction sites which permit easy manipulation of the gene to replace coding sequence portions with these encoding analogs.

Correct ligations for plasmid construction can be confirmed by first transforming E. coli strain MM294 obtained. from E. coli Genetic Stock Center, CGSC #6135, or other suitable host, with the ligation mixture. Successful transformants can be selected by ampicillin, tetracycline or other antibiotic resistance or by using other markers depending on the mode of plasmid construction, as is understood in the art. Plasmid from the transformants are then prepared, optionally following chloramphenicol amplification. The isolated DNA is analyzed by restriction and/or sequenced by the dideoxy method of Sanger, F., et al., Proc. Natl. Acad. Sci. USA (1977) 74:5463 as further described by Messing, et al., Nucleic Acids Res. (1981) 9:309, or by the method of Maxam, et al., Methods in Enzymology (1980) 65:499.

The constructed vector is then transformed into a suitable host for production of the protein. Depending on the host cell used, transformation is done using standard techniques appropriate to such cells. The calcium treatment employing calcium chloride, as described by Cohen, S. N., Proc. Natl. Acad. Sci. USA (1972) 69:2110, or the RbCl method described in Maniatis, et al., Molecular Cloning: A Laboratory Manual (1982) Cold Spring Harbor Press, p. 254 is used for procaryotes or other cells which contain substantial cell wall barriers. For mammalian cells without such cell walls, the calcium phosphate precipitation method of Graham and van der Eb, Virology (1978) 52:546 or electroporation is preferred. Transformations into yeast are carried out according to the method of Van Solingen, P., et al., J. Bacter. (1977) 130:946 and Hsiao, C. L., et al., Proc. Natl. Acad. Sci. USA (1979) 76:3829.

The transformed cells are then cultured under conditions favoring expression of the MHC sequence and the recombinantly produced protein recovered from the culture.

MHC-Binding Peptides

It is believed that the presentation of antigen by the MHC glycoprotein on the surface of antigen-presenting cells (APCs) occurs subsequent to the hydrolysis of antigenic proteins into smaller peptide units. The location of these smaller segments within the antigenic protein can be determined empirically. These MHC-binding peptides are thought to be about 8 to about 10, possibly about 8 to about 11, or about 8 to about 12 residues in length, and contain both the agretope (recognized by the MHC molecule) and the epitope (recognized by T cell receptor on the T cell). The epitope is a contiguous or noncontiguous sequence of about 5-6 amino acids that is recognized by the antigen-specific T cell receptor. The agretope is a continuous or noncontiguous sequence that is responsible for binding of the peptide with the MHC glycoproteins. The invention provides systems, kits, and assays for evaluating putative MHC-binding peptides to determine whether such fragments can be incorporated into a ternary complex with an MHC monomer or modified MHC monomer.

Thus, the invention provides systems, kits and screening methods to be used in screening of candidate peptides for use in diagnostic assays, vaccines, and other treatment modalities. Putative MHC-binding peptides for use in the invention methods can be made using any method known in the art, the most convenient being peptide synthesis for fragments of 8 to 12 amino acids in length.

Accordingly, in one embodiment the invention provides a system comprising a solid surface having attached thereto one or more MHC monomer or modified MHC monomer wherein the monomer denatures in a denaturing condition and reconstitutes to form a functional binding pocket containing a suitable MHC-binding peptide under reconstituting conditions. For example, a plurality of the monomers can be bound to a single surface. The surface of the system can be any known or later discovered solid surface including, without any limitation, any solid, polymer, membrane, synthetic surface, and the like. For example, the solid surface of the invention system can be a microtiter plate, such as the wells of a microtiter plate, or a bead, such as an agarose A bead, an agarose G bead, and the like. In one aspect, the solid surface of the invention system is suitable for use in a high throughput scanning system, e.g., the surface is compatible with the high throughput system or allows a system to work with the entities associated with the surface in a high throughput manner, such as fluorescence determined flow cytometry.

Recently, a short peptide sequence (streptagII) has been identified that demonstrates binding affinity (Kd~1×10-6M) for the biotin-binding site of a mutated streptavidin molecule, called STREPTACTIN®. The molecule d-biotin, which binds with higher affinity to STREPTACTIN® (Kd~1×10-13 M) effectively competes with the StrepTagII for the binding site. (Knabel, M., Franz, T. J., Schiemann, M., Wulf, A., Villmow, B., Schmidt, B., Bernhard, H., Wagner, H., Busch, D. H. (2002) Reversible MHC multimer staining for functional isolation of T-cell populations and effective adoptive transfer. Nature Medicine Vol. 8 No. 6, June 2002. pp: 631-637). Attachment of the MHC monomers to the solid surface can be accomplished by any method known in the art. For example, the solid surface can be coated with a first binding ligand, such as avidin, and the monomer is then provided with a second binding ligand, such as biotin, wherein the first ligand binds specifically with the second ligand. The second binding ligand may optionally be attached to the monomers via a C-terminal end. Attachment of the one or more monomers to the solid surface is optionally reversible or cleavable. For example, a cleavable binding complex is commercially available from Amersham Bioscience Bioscience (Orsay France) such as Factor Xa, PRESCISSION® Protease and thrombin. All of these proteases can be used with the GST affinity tag from proteins expressed using pGEX-T vectors.

The invention system comprising a solid support with attached MHC monomers is preferably stored in a renatured state, by causing formation of a ternary complex with the MHC monomer containing a MHC binding peptide of 8 to 12, or about 9 to 11 amino acids in the binding pocket and a beta-2 microglobulin molecule bound thereto, as described herein.

Formation of the ternary complex containing a MHC heavy chain or modified MHC attached to a solid support is referred to herein as "renaturation" and is accomplished under renaturing conditions as is know in the art and described herein. For example, renaturing conditions typically include the presence of a suitable MHC binding peptide for the monomer, the presence of beta-2 microglobulin, and a suitable refolding buffer having a pH of from about 7 to about 8.5. Suitable refolding buffers are illustrated in the Examples herein and are known in the art.

In further preparation for storage, the solid support with bound MHC monomer(s) can be dried while in a renatured state, for example by exposure to a buffer containing sugars. In preparation for use of the solid support of the invention system to test putative MHC-binding peptides, the solid support and attached MHC monomers in ternary complex are exposed to denaturing conditions to cause dissociation and unfolding of the monomers. For example, denaturing conditions can comprise exposure of the solid support and bound monomers to a pH of about 2 to about 4 for sufficient time to cause dissociation of the ternary complexes without damage to the monomers.

Optionally, the invention system may further comprise a monoclonal antibody, described in greater detail below, that binds specifically to a conformational epitope that is present in the ternary complex and absent in the dissociated components of such a complex. For example, the conformational epitope may be formed in the reconstituted MHC monomers or modified MHC monomers used in the system and absent in the denatured monomers. The invention system may further contain a supply of beta-2 microglobulin.

The MHC monomer used in the invention systems and methods can be any MHC monomer or modified MHC monomer, i.e., class I heavy chain, capable of binding a peptide in the range of 8 to 11 amino acids, for example 8 to 10 amino acids under renaturing conditions. The MHC monomer can be encoded by any partial or full-length modified or unmodified MHC gene sequence from any species or subtype, or a combination thereof, including without limitation human and murine species, and chimera thereof. Preferred MHC encoding gene sequences are those encoding any HLA allele genotype and any variation or polymorphism thereof. For example, the MHC monomer utilized in the invention systems and methods can be any partial or full-length HLA heavy chain that binds an HLA-binding peptide under renaturing conditions, i.e., any subtype or allele of HLA-A, HLA-B, or HLA-C, For example, in one embodiment, the MHC monomer is modified by truncation to include only the $\alpha_1$, $\alpha_2$ and the $\alpha_3$ domains of an HLA heavy chain. In still another embodiment, the MHC monomer can be a chimeric, such as a fusion protein, containing these MHC domains and an anchor domain, wherein the MHC domain binds to a MHC-binding a peptide, as described herein, while the anchor domain is suitable for immobilizing the MHC monomer to a surface. The anchor domain can be a polypeptide fused with the HLA domain to form a fusion protein or can be any entity coupled to the HLA domain through any suitable means known in the art, e.g., biotinylated MHC monomer.

The MHC monomer can be attached to the solid surface by any suitable means known in the art. For example, the MHC monomer can be immobilized to a surface either directly or indirectly, e.g., via an anchoring or connecting entity. In one embodiment, the solid surface of the invention system is coated with a first ligand entity, which binds to or interacts with a second ligand connected to or within the MHC monomer, e.g., via covalent or noncovalent bond. In another embodiment, the surface is coated with avidin or its derivatives, e.g., streptavidin, and the MHC monomer contains biotin or its derivatives as its anchor domain. Attachment of the MHC monomer to the solid surface, in one embodiment of the invention, is reversible or cleavable.

The MHC monomer coated or immobilized to a solid surface can be denatured, e.g., stripped or dissociated in a denaturing condition, and then renatured, e.g., refolded from a denatured form under a non-denaturing or renaturing condition so as to bind an appropriate MHC-binding peptide. In one embodiment, the surface coated with the MHC monomer provided by the present invention can be dried and stored for use at a later time. Preferably, the storage is at 4 degrees C.

In addition to the surface coated with the MHC monomer the system of the invention can further include a monoclonal antibody and a peptide. The peptide can be any peptide that binds to the HLA heavy chain monomers, e.g., MHC-binding peptides. In one embodiment, the peptide has high affinity to the MHC monomer, e.g., HBc high affinity peptide.

The monoclonal antibody used in the invention systems and methods can be any monoclonal antibody that specifically binds to a conformational epitope present only in a ternary complex of an MHC monomer and not present in dissociated components of the ternary complex. For example, the conformational epitope can be present in beta-2 microglobulin when incorporated into the ternary complex. Alternatively, the monoclonal antibody can recognize a conformational epitope present in the MHC monomer or modified MHC monomer being used in a particular invention system or method. The monoclonal antibody may be species-matched to the MHC monomers, for example, when the solid support has attached HLA class I monomers, the monoclonal antibody is a murine, human or humanized anti-MHC class I monoclonal antibody. However, when the modified MHC monomer is a chimera containing domains from more than one species, the anti-MHC monoclonal antibody can be selected to bind to a conformational epitope present in only one of the domains. For example, as illustrated in FIG. 9, a ternary complex containing modified MHC monomer that is a chimera containing alpha-1 and alpha 2 domains of HLA-A2 heavy chain and a murine alpha-3 domain of H-2 Kb can be detected by a murine monoclonal antibody that binds to a conformational domain in the murine alpha-3 domain.

When the MHC monomer is an HLA monomer, the monoclonal antibody can be any anti-MHC class I monoclonal antibody that recognizes any subclass of HLA monomer in a ternary complex, i.e., HLA-A, HLA-B or HLA-C. A preferred anti-MHC-class I monoclonal antibody for use in the invention systems and methods is a mouse IgG2a conformational dependent anti-HLA monoclonal antibody produced by hybridoma B9.12.1, which as been deposited under the provisions of the Budapest Treaty on the International Recognition of the Deposit of Microorganisms for the Purpose of Patent Procedure and the Regulations thereunder (Budapest Treaty) at Collection Nationale de Cultures de Microorganismes (CNCM), Institut Pasteur 25, Rue du Docteur Roux, F75724 Paris Cedex 15 France, under registration number CNCM 1-2941. This assures maintenance of viable cultures for 30 years from the date of deposit. The organisms will be made publicly available by CNCM under the terms of the Budapest Treaty and assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

In one embodiment, the monoclonal antibody used in the invention systems and methods is provided with a detectable label, i.e., a label that produces a detectable signal as is known in the art. Labels may be conjugated to the antibody using any of a variety of procedures known in the art. Alternatively, the antibody can be produced to include a label, such as a radioactive amino acid. Labels suitable for use in the invention systems, kits and methods include, but are not limited to, radioisotopes, fluorochromes, enzymes, biotin and electron dense molecules. Binding of the monoclonal antibody indicates formation of a ternary complex by binding of a MHC-binding peptide to the monomer and can be easily detected and/or quantified by detecting the signals produced by the signal entity after washing away unbound antibody and other components of the system. A detectable label presently preferred is a fluorescent label, e.g., FITC. The binding of fluorescently labeled antibodies on the solid support can be readily detected using a fluorimeter or by fluorescence determined flow cytometry.

The invention system can be provided either as part of another system or as a kit. For example, microtiter plates coated with the MHC monomers or modified monomers, e.g., in dried form, can be provided in a kit, which can optionally additionally include, in separate vials or containers, an anti-MHC monoclonal antibody or an anti-beta-2 microglobulin antibody, as described herein, and a control peptide that binds specifically to the monomers attached to the solid support. In one embodiment, the kit includes an instruction explaining the procedures for using the system to conduct immunoassays, e.g., the methods provided by the present invention. The kit can optionally also include any or all of the following: denaturing or refolding buffers, controls for the MHC monomers, the peptide, or the monoclonal antibody.

In yet another embodiment, the invention provides methods for determining binding between a MHC monomer or modified MHC monomer and a putative MHC-binding peptide to be tested for binding to the monomer(s). In this method for assaying binding of a putative MHC-binding peptide, a solid surface having attached thereto a plurality of MHC monomers or modified MHC monomers is incubated in the presence and absence of the putative MHC-binding peptide. Preferably the solid surface is one belonging to an invention system or kit and is prepared as described herein. If the MHC monomers attached to the solid support at the start of the assay procedure are in a reconstituted form, the MHC monomers are prepared for the assay by exposure to denaturing conditions as described herein, for example by exposure to a pH in the range from about 2 to about 4, or exposure overnight to a temperature higher than about 37° C. After denaturation, unbound MHC-binding peptides are washed away.

For the assay, the solid support with attached denatured MHC monomers or modified MHC monomers is incubated with a putative MHC-binding peptide under reconstituting conditions for a suitable period of time to allow for formation of ternary complexes. The reconstituting conditions will include the presence of a sufficient amount of beta-2 microglobulin (or beta 2 microglobulin modified to increase binding or stabilize ternary complex formation) to saturate the MHC monomers. For example, it is contemplated that the beta 2-microglobulin may be modified by attachment thereto of a stabilizing molecule, such as a leucine zipper, or the like, to stabilize ternary complex formation. Incubation with the putative MHC-binding peptide and beta-2 microglobulin will typically be required from about 12 hours or overnight to about 48 hours to allow for complex formation. The reconstituting conditions may also include a temperature in the range from about minus 18° C. to about 37° C., for example about 4° C. to about 8° C.

After the reconstituting incubation, binding to the MHC monomers of the putative MHC-binding peptide is determined by contacting the MHC monomers on the solid support with a monoclonal antibody that binds to a conformational epitope present only in ternary complex, for example a conformational epitope present in the refolded MHC monomer of the ternary complex and not present in a denatured MHC monomer. Binding of the antibody with the ternary complex attached to the solid support indicates that the putative MHC-binding peptide is an MHC-binding peptide specific for the MHC monomers or modified MHC monomers used in the assay. For purposes of comparison of the binding of the putative MHC-binding peptide to that of a standard MHC-binding peptide, a parallel assay (e.g., under the same reconstituting conditions, same monomer, and in the presence of the same monoclonal antibody) may be conducted using the monomers. Binding of the monoclonal antibody in the parallel assay to the ternary complex containing the standard MHC-binding peptide can be compared to binding of the monoclonal antibody to the ternary complex in the test assay to aid in determining the binding efficiency of the putative MHC-binding peptide, using computational methods known in the art.

In still another embodiment, the invention provides methods for determining the degree of binding affinity of an MHC monomer or modified MHC monomer for a putative MHC-binding peptide. In this embodiment, at least one denatured MHC monomer or modified MHC monomer attached to a solid surface is incubated under reconstituting conditions with the putative MHC-binding peptide and a monoclonal antibody that specifically binds to a conformational epitope created by formation of a ternary complex containing a corresponding reconstituted MHC monomer that is not present in any of the dissociated components of the complex. For reconstitution, a suitable amount of beta-2 microglobulin for complex formation of the total amount of monomer in the assay must also be present Binding of the monoclonal antibody to the ternary complex so formed, is compared with binding of the monoclonal antibody to a corresponding ternary complex containing the same MHC monomer or modified MHC monomer and a known MHC-binding peptide. The difference in the binding indicates the relative degree of binding affinity of the reconstituted MHC monomer or modified MHC monomer for the putative MHC-binding peptide. For the determination of the binding affinity of a peptide the test is done in multiples using different peptide concentrations in each parallel test. In practice of the invention methods, the MHC monomers may belong to any species for which determination of appropriate class I binding peptides is desired, including, without limitation, murine and human or a chimera containing monomer subunits from a combination of species or subtypes.

Various readily available means can be used to determine the specific binding of the monoclonal antibody to the ternary complex containing the reconstituted MHC monomer. For example, the binding can be detected by directly labeling the monoclonal antibody with a detectable label, i.e., one that produces a detectable signal, and detecting the signal or via a secondary antibody which is detectably labeled and recognizes the monoclonal antibody that binds to the ternary complex containing the MHC monomer used in the assay. Suitable detectable labels that can be used for this purpose are well known in the art and include labels selected from the group consisting of radioisotopes, fluorochromes, enzymes, biotin, electron dense molecules, and the like. Fluorochromes or fluorescent labels are currently preferred since binding can readily be detected by subjecting the solid support to a fluorimeter. For example, when the solid support is a plate, such as a 96 well microtiter plate, or beads, such as agarose A or agarose G beads, the assay can take advantage of high through-put florescence scanning using any of the methods known in the art.

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Detection of Correctly Folded HLA Heavy Chain Monomers

Figure 1:
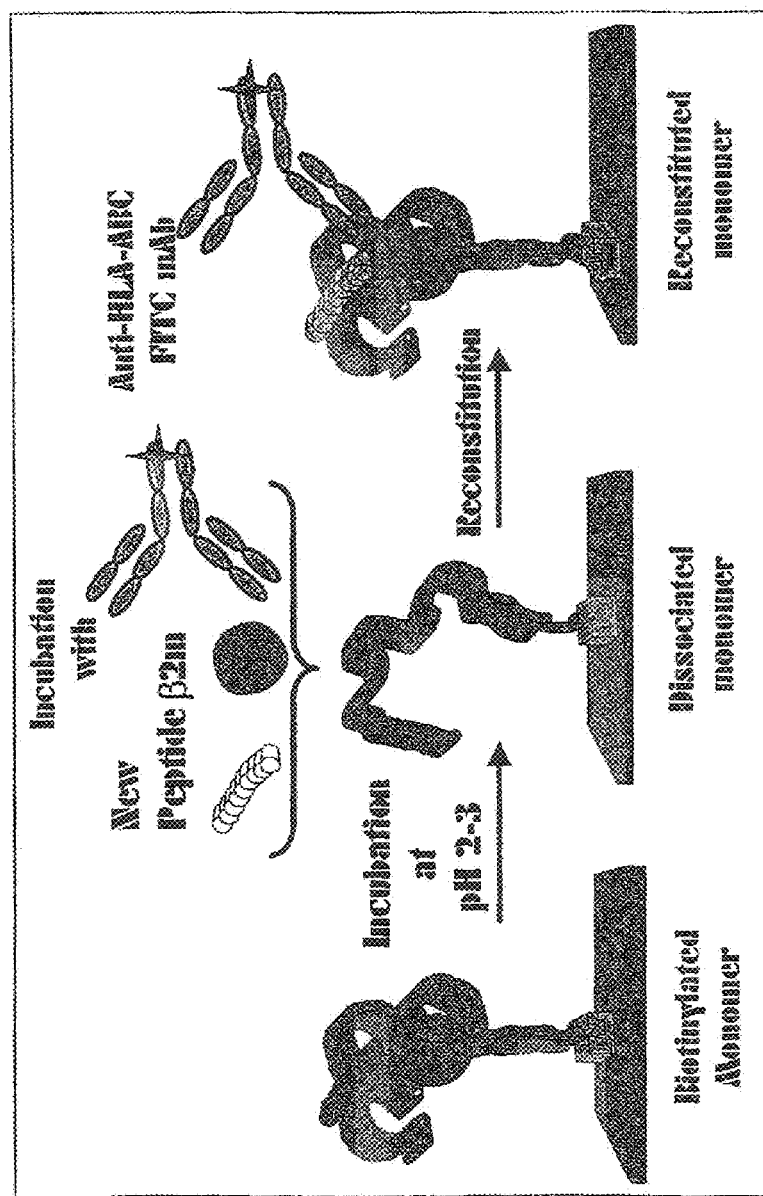
FIG. 1 is a schematic representation of the immunoassay.

This experiment demonstrates that MHC monomers when attached to a solid support can be reconstituted so as to form a ternary complex and be recognized and specifically bound by a conformation-dependent anti-MHC monoclonal antibody. In other words, MHC monomers bound to a solid support will correctly fold to bind MHC-binding peptides. Table 1 below summarizes the major steps for detecting the correctly folded HLA monomers upon peptide binding. (See also FIG. 1.)

TABLE 1

| Step 1 | Step 2 | Step 3 |
|---|---|---|
| Incubation of HLA heavy chain coated plates with low pH solution. Washing | After washing, incubation with different concentrations of peptide and a constant concentration of beta-2 microglobulin and anti-HLA-class I-FITC mAb. Incubation time: overnight or 24 h | Washing and read out in the fluorimeter |

Example 2

Calibration of Anti-HLA-FTIC Antibody

In this example BSA-Biotin-Avidin coated 96-well microtiter plates were prepared used for a fluorimetric assay. HLA-A2m monomer in ternary complex with binding peptide Mart-1 26-35L was incubated at various concentrations with an anti-HLA-ABC-FITC or anti-HLA-FITC monoclonal antibody at concentrations of 0, 0.25, 0.5, 1, 2, and 4 µg/ml. Specifically, for each antibody concentration, the HLA monomer was added at concentrations of 0, 0.0078, 0.0156, 0.03125, 0.0625, 0.125, 0.25, and 0.5 µg/ml.

In this experiment the HLA heavy chain and the anti-HLA-FITC antibody were incubated together for 40 min at room temperature under shaking. The total fluorescence was read before washing the plates to remove unbound antibody. Then, plates were washed three times to remove any unbound antibody, and the fluorescence of the bound monomers was read.

Figure 2:
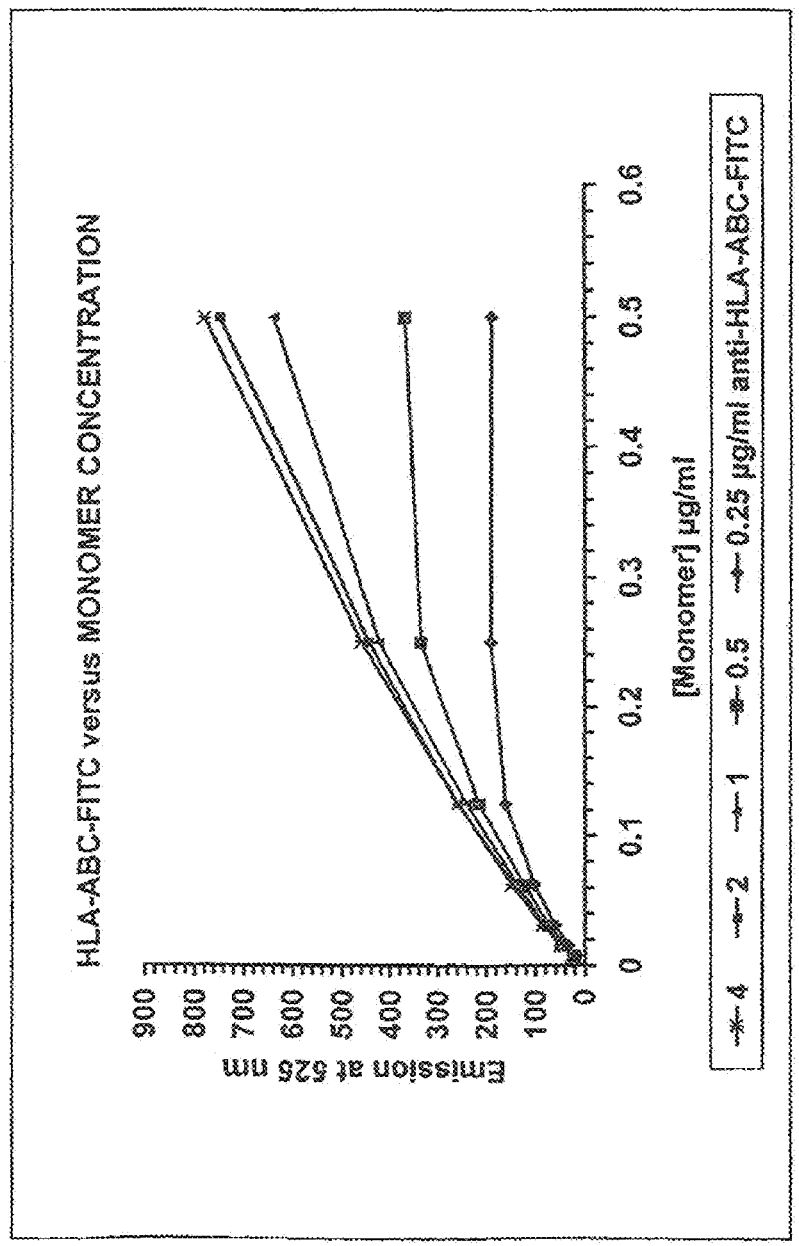
FIG. 2 is a graph showing calibration of the anti-HLA-class I-FITC mAb for fluorometric assay.

As shown in FIG. 2, saturation occurred when the antibody concentration reached 0.25 and 0.5 µg/ml. However, the fluorescence signal increased when the antibody was added at 1, 2 and 4 µg/ml. This observation indicates that the antibody binds two MHC monomers when added at 0.5 and 0.25 µg/ml. In contrast, upon incubation at 1, 2 or 4 µg/ml, the antibody binds only one HLA monomer. This explains the signal increase, e.g., 300 Fluorescence units (FU) with 0.5 µg/ml of antibody and 0.5 µg/ml of HLA heavy chain as compared with 600 FU with 1 µg/ml of antibody and 0.5 µg/ml of HLA heavy chain. Another observation was that between the concentrations of 2 and 4 µg/ml of antibody the signal remains constant. It was determined, therefore, that 2 µg/ml of anti-HLA-FITC mAb was an appropriate saturation concentration to use for the assay.

Example 3

Specificity of Anti-HLA-FITC Monoclonal Antibody

A. Conformational Specificity

Experiments were designed to determine if the signal produced from anti-HLA-class I-FITC antibody differs as a function of the degree of dissociation of a stressed HLA monomer. The particular HLA monomer used for the experiments was HLA heavy chain monomer HLA-A*0201 containing binding peptide Mart1 27-35 in ternary complex.

Different solutions containing the ternary complex at a concentration of 10 µg/ml were prepared and incubated overnight at the temperatures of 37° C., 30° C., 25° C., or 4-8° C. Antibody binding experiments as described above in Example 2 were carried out using 2 µg/ml of anti-HLA-FITC conjugate to detectably label the HLA monomers remaining in ternary complex attached to the solid support. A solution containing a ternary complex of HLA monomer and Mart 1 27-35 at a concentration of 640 µg/ml were incubated at −18° C. as a control. A solution, from a sample stored at −18° C. at the concentration of 640 µg/ml, containing a ternary complex of HLA-monomer and Mart-1 27-35 was diluted at the same concentration than the other samples and included as control.

Figure 3:
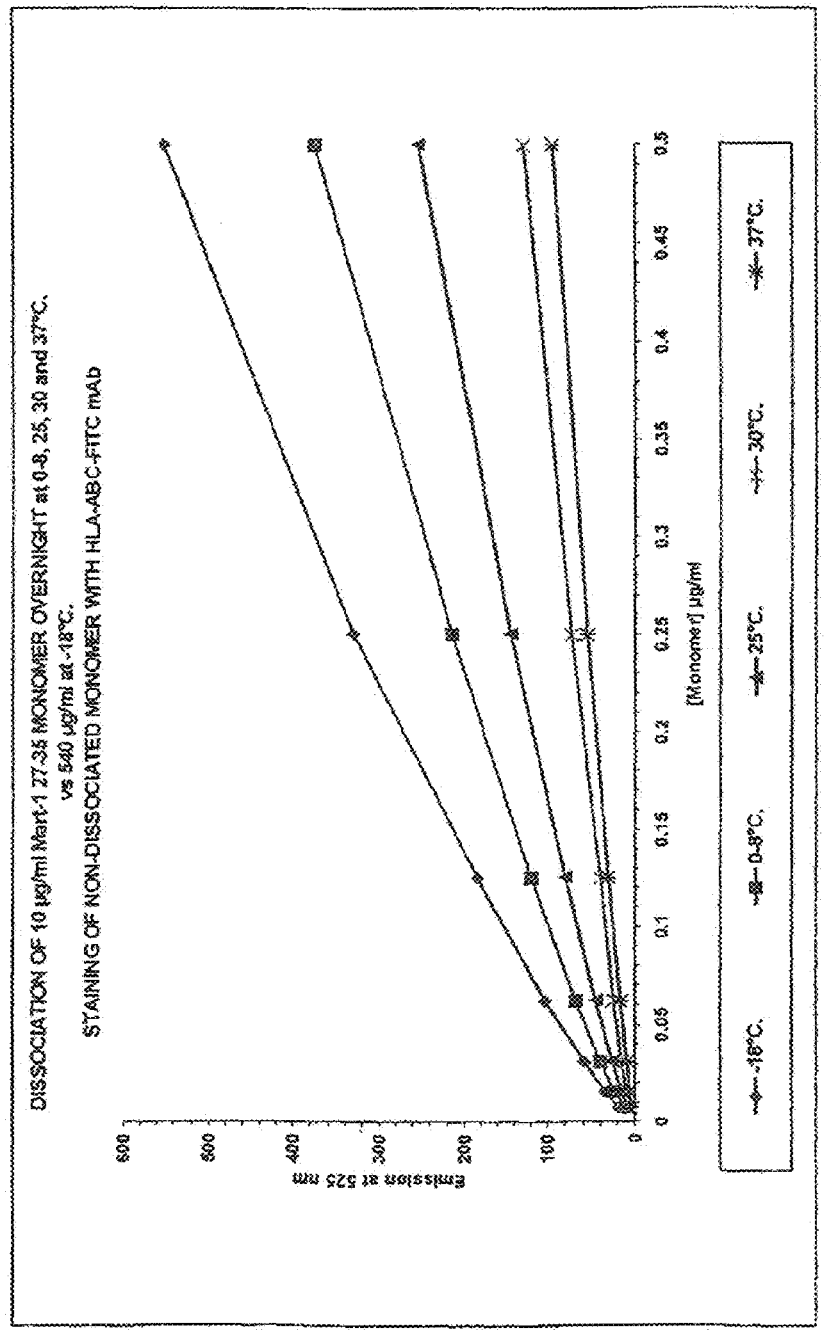
FIG. 3 is a graph showing a decrease in binding of anti-HLA-class I-FITC mAb to a reconstituted HLA heavy chain monomer Mart1 26-35 with increasing temperature as determined by fluorescence of bound antibody.

As shown in FIG. 3, it was found that incubation of the ternary complex bound to the solid support at highest temperature gave the weakest fluorescent signal, indicating that the ternary complex of HLA heavy chain monomer gradually dissociated as the temperature was increased. At one point, the anti-HLA-FITC conjugate could no longer recognize the HLA monomer because of the degree of dissociation of the ternary complex dissociation and the fluorescence signal diminished accordingly, indicating that the anti-HLA-FTIC conjugate specifically recognizes correctly folded reconstituted HLA monomers, but not denatured monomers.

B. Heavy Chain Monomer Specificity

As shown in Table 2, different HLA heavy chain monomers for human alleles, A2, A3, A11, B7, B8, as well as one mouse allele Kd were incubated with the anti-HLA-Class I-FITC antibody.

TABLE 2

| Human alleles | Mouse allele |
|---|---|
| HLA-A*0201/Mart1 2635L | H-2Kd/Flu |
| HLA-A*0301/EBV | |
| HLA-A*1101/EBV | |
| HLA-B*0702/gp41 | |
| HLA-B*0801/Nef | |

The antibody binding experiments were carried out as described above. The concentration of the anti-HLA-class I-FITC antibody used was 2 µg/ml.

Figure 4:
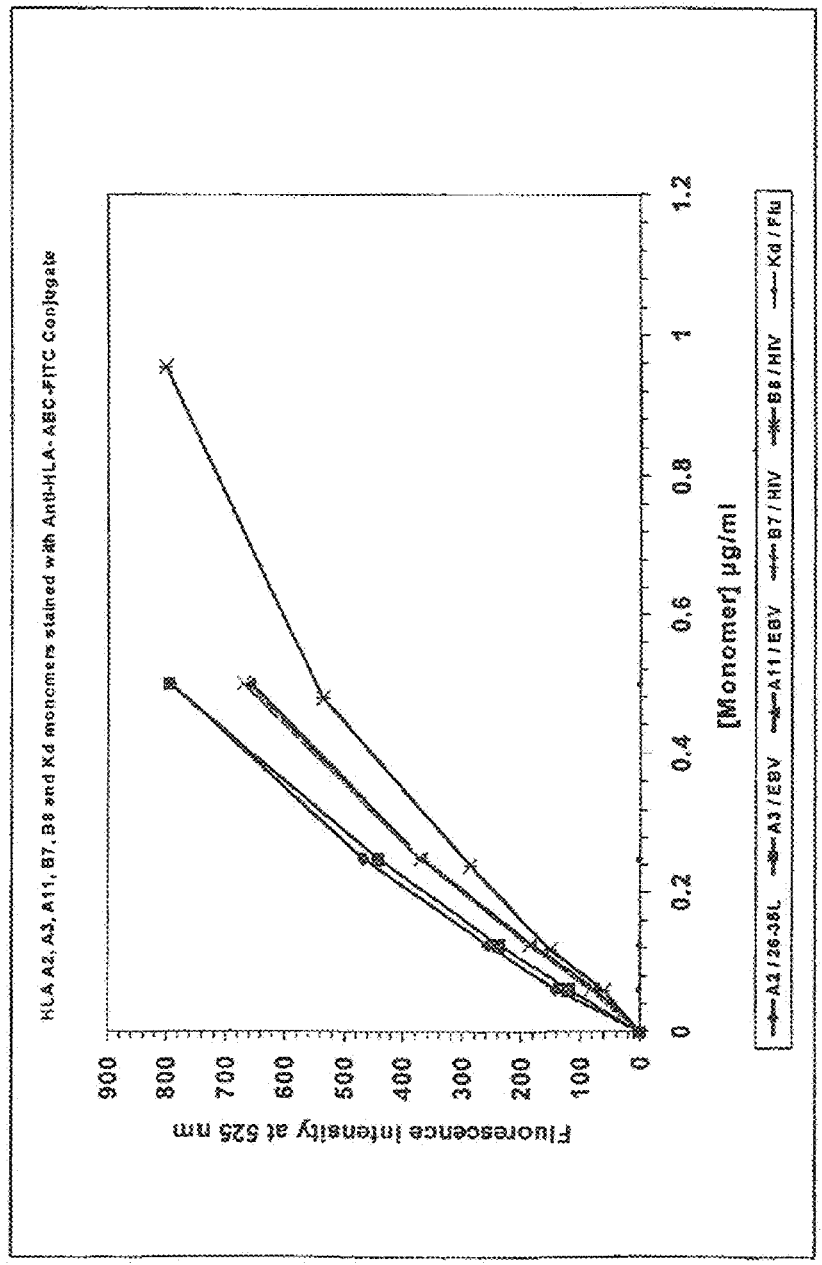
FIG. 4 is a graph showing the binding of an anti-HLA-class I-FITC monoclonal antibody to human and mouse alleles as determined by fluorescence of bound antibody.

As shown in FIG. 4, all the reconstituted HLA-A and -B monomers were detectable with the anti-HLA-class I monoclonal antibody. As expected, no signal was detected when a ternary complex containing the mouse allele (H-2 Kd/Flu) was attached to the plate, confirming the specificity of the antibody to human HLA. Variations of signal between different alleles were likely due to concentration precision and storage conditions of the HLA monomers, e.g., freeze, thaw, etc.

Coating of MHC Heavy Chain Monomers to Plates, Plate Storage and Reconstitution

Biotinylated MHC monomers in a ternary complex with Mart1 27-35 peptide at the concentration of 5 µg/ml were attached to avidin coated plates. After saturating the plates with a sugar-containing buffer overnight at 4° C. to 8° C., the plates were dried overnight at 30° C. and 19% humidity. After the plates were dried under these conditions, it was found that the HLA monomers were dissociated from the ternary complex. Therefore, it was not necessary to strip the MHC-binding peptide from the monomers with low pH in preparation for use of the plates in the binding assay.

For the antibody binding assay, 10 nM to 100 µM of HBc high affinity peptide (the affinity can be calculated as $1.8\times10^{-7}$M) were incubated with 10 µg/ml of β2 microglobulin and the monomer-coated plates were incubated with one of the three different buffers containing ingredients as described below:

Buffer 1: Tris, Arginine, EDTA, GSH, GSSG and BSA
Buffer 2: Tris, NaCl, EDTA, $NaN_3$, BSA and 0.05% TWEEN 20® detergent
Buffer 3: Tris, NaCl, EDTA, $NaN_3$, BSA and 0.05% NONIDET® P40 detergent.

It was found that peptide binding and reconstitution of the monomers occurred at 2 temperatures: 4° C.-8° C. and room temperature.

Figure 5:
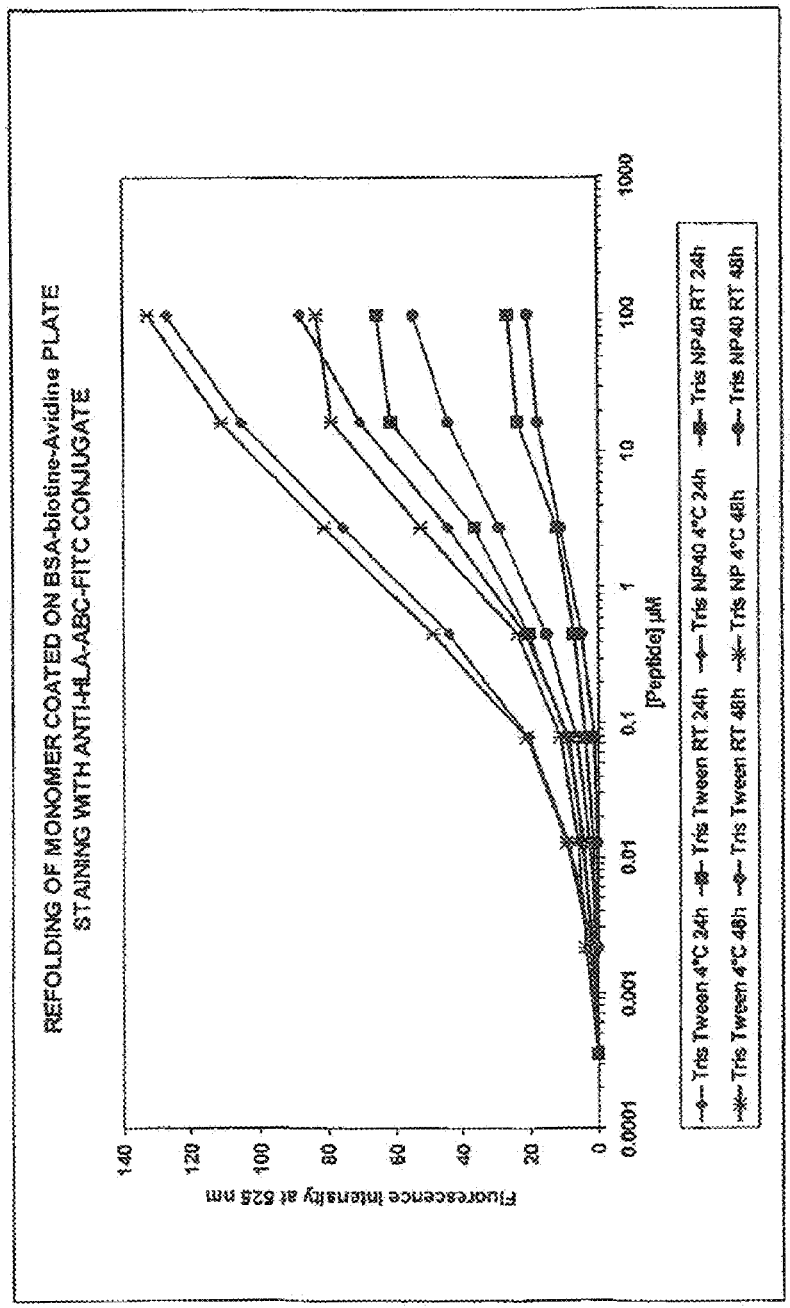
FIG. 5 is a graph showing renaturation in various buffer solutions of the MHC heavy chain monomers attached to a plate as detected by an anti-HLA-class I-FITC mAb.

Renaturation of the HLA monomers was tested after 24 hours and 48 hours of incubation with 2 µg/ml of anti-HLA-class I-FITC conjugate. As shown in FIG. 5, the FITC signal increased as a function of the peptide concentration. This result shows that the HLA monomer renaturated by incorporation into a ternary complex and that renaturation of MHC monomers can be effectively detected with an anti-HLA-class I-FITC antibody. It was found that the best renaturation buffer was the Buffer 2 containing TWEEN 20®. Interestingly no refolding was measured with Buffer 1.

Under the conditions tested here, the best temperature for the antibody binding assay was 4° C.-8° C. and the best incubation period to allow renaturation was 24 hours.

Material and Methods

A. Reagents.

Fine chemicals, unless otherwise stated, were from Merck (Darmstadt, Germany) and CarloErba (Rodeno, Italy). Biotinylated BSA as well as avidin was obtained from Immunotech (Marseille, France). LUMITRAC-600 White 96-well microtiter plates were from Greiner [PN: 655074 LUMITRAC 600; (Frickenhausen, Germany). SA-PE as well as HLA-A*0301/EBV HLA heavy chain were from Immunomics ((San Diego, Calif.). Anti-IILA-class I monoclonal antibody conjugated to FITC (clone: B9.12.1) was from Antibody Manufacturing Service of Immunotech. Part Number: IM1838. This antibody is a mouse IgG2a monoclonal antibody.

B. Preparation of Avidin Coated 96-Well Microtiter Plates.

Each well of white 96-well microtiter plates were coated with 200 µl of a 5 µg/ml biotinylated BSA solution in PBS and the plates were incubated for 16 hours at 4° C. The plates were washed and then 200 µl/well of avidin solution at 5 µg/ml was added. The plates were then incubated for another 16 hours at 4° C. Subsequently the plates were washed and a blocking, drying solution was added. The plates were incubated again for another 16 hours. Afterwards, the solution was poured off and the plates were slapped face down on paper towels. Then the plates were placed in a special drying room for 24 hours. Afterwards the plates were placed individually in a self-locking bag until use.

C. Monomer Immunoassay Procedure.

The assay procedure was as follows. Each sample 200 µl/well containing the HLA monomer in ternary complex at 0.25 µg/ml and diluted in Tris 10 mM, NaCl-150 mM, EDTA 0.5 mM, $NaN_3$ 0.1%, BSA 0.2%, was loaded into wells of the avidin-coated plate and incubated for 1 hour at room temperature on an orbital shaker in the dark. The wells were then rinsed three times with an automatic washer (SLT, Salzburg, Austria) using 300 µl of a 9 g/l NaCl solution containing 0.05% TWEEN 80®. Subsequently 200 µl/well of FITC-conjugated anti-HLA-class I antibody at 2 µg/ml were added. The plates were incubated for 45 min at room temperature on an orbital shaker in the dark, washed three times, and 200 µl/well of Tris 10 mM, NaCl-150 mM, EDTA 0.5 mM, NaN3 0.1%, BSA 0.2% were added. The FITC fluorescence was measured with a Perkin Elmer LS-50B fluorimeter following these parameters:

Excitation=405 nm
Emission=525 nm
Emission filter=515 nm
Band pass (Exc,Emi)=5.15 nm
0.5 sec/well The assay procedure is further summarized in Table 3 below.

TABLE 3

| Step 1 | Step 2 | Step 3 | Step 4 |
| --- | --- | --- | --- |
| Mix IILA heavy chain and streptavidin PE | Incubate 200 µl/well of each sample in the 96-well streptavidin coated white plates. Incubate 1 hour at room temperature in the dark under agitation | Three washes Add 200 µl/well of anti-HLA-class I mAb at 2 µg/ml Incubate 45 min at room temperature in the dark under agitation | Three washes Add 200 µl of buffer Fluorescence determination |

Calibration of the Anti-HLA-Class I-FITC Antibody

Figure 6:
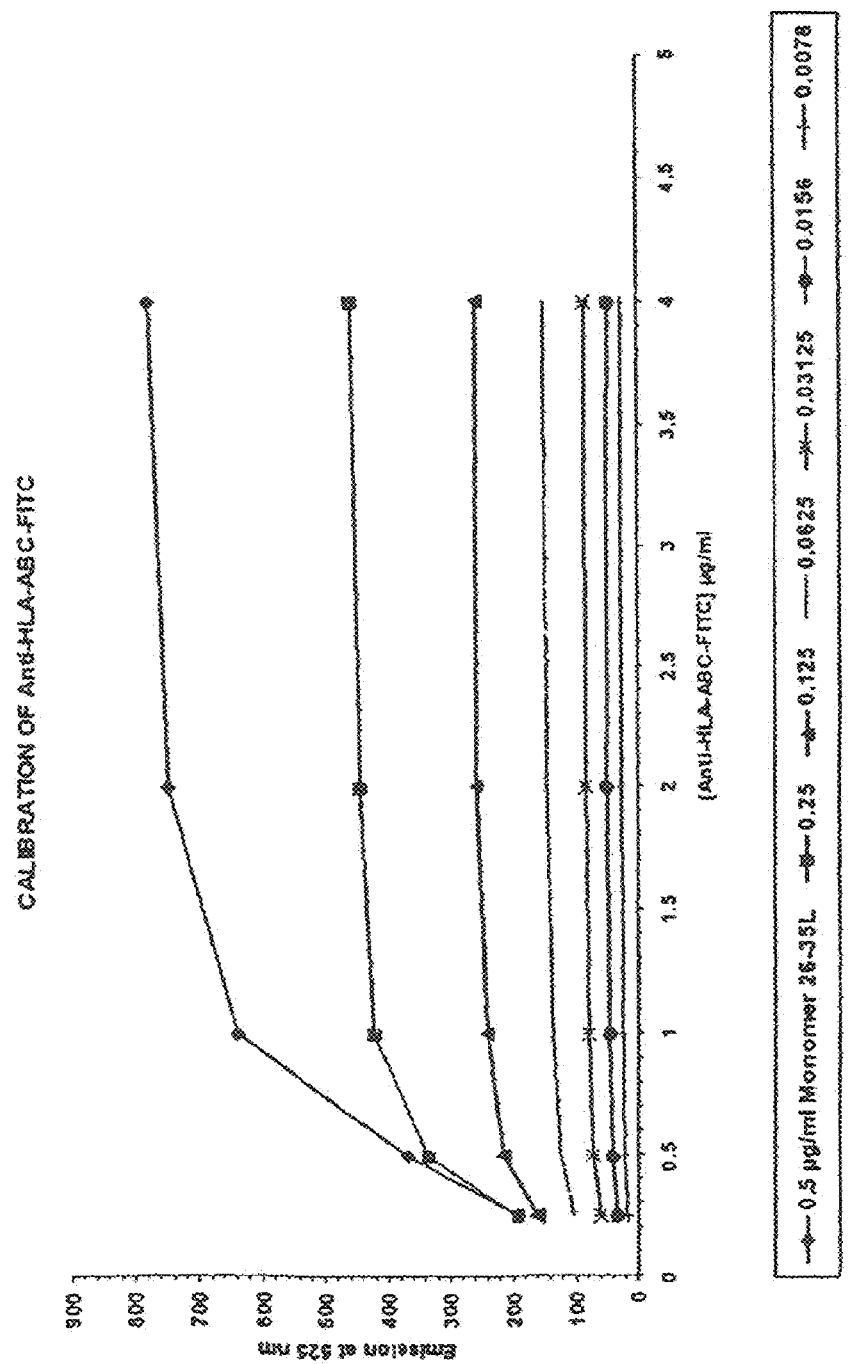
FIG. 6 is a graph showing antibody binding to monomer at concentrations of anti-HLA-class I mAb of 1 to 2 µg/ml for various HLA heavy chain monomer concentrations to determine the optimal concentration of the anti-HLA-class I antibody for use with a microtiter plate assay.

HLA-A*0201/Mart1 reconstituted monomers in various concentrations was incubated with various concentrations of the anti-HLA-class I-FITC mAb. As shown in FIG. 6, a plateau was reached with concentrations of anti-HLA-class I mAb at 1 to 2 µg/ml for all HLA heavy chain monomer concentrations.

Figure 7A:
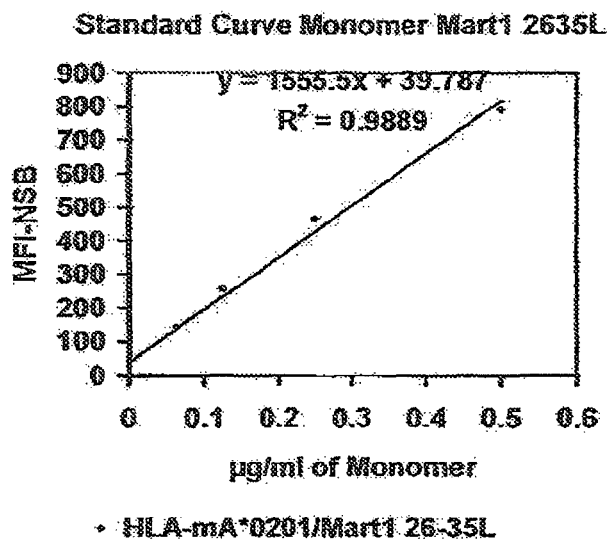
FIGS. 7A and 7B are graphs showing the dose response curve obtained with two different HLA heavy chain monomers
Figure 7B:
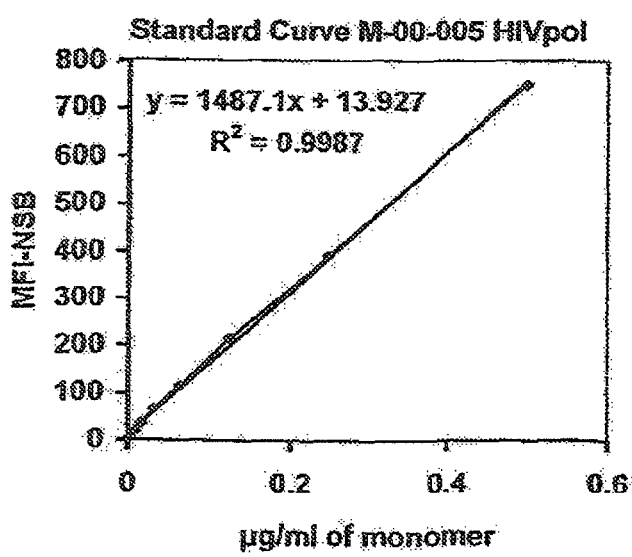

A dose response curve at various concentration of reconstituted monomers was plotted using 2 µg/ml of anti-HLA-ABC mAb. As shown in FIGS. 7A and 7B, the signal remained linear with increasing concentrations until 0.5 µg/ml of reconstituted HLA monomer was used. Concentrations of the reconstituted HLA monomer higher than 0.5 µg/ml provided signals that were very close to a plateau. The data summarized in FIGS. 7A and 7B demonstrate that for the best result, the assay conditions should include 0.25 µg/ml of reconstituted HLA monomer and 2 µg/ml of anti-HLA-class I FITC mAb. These data also indicated that the sensitivity of the assay is about 4 to 6 ng/ml of the reconstituted HLA monomer.

Specificity

The specificity of the anti-HLA-class I-FITC antibody for HLA monomer in ternary complex was tested against different human alleles. A dose response curve was prepared as described above for each of the following HLA monomer/peptide ternary complexes.

HLA-A*0201/Mart1 2635L
HLA-A*0301/EBV
HLA-B*0702/HIV
HLA-B*0801/HIV
HLA-A-*1101/EBV
H-2 Db/HA1

Figure 8:
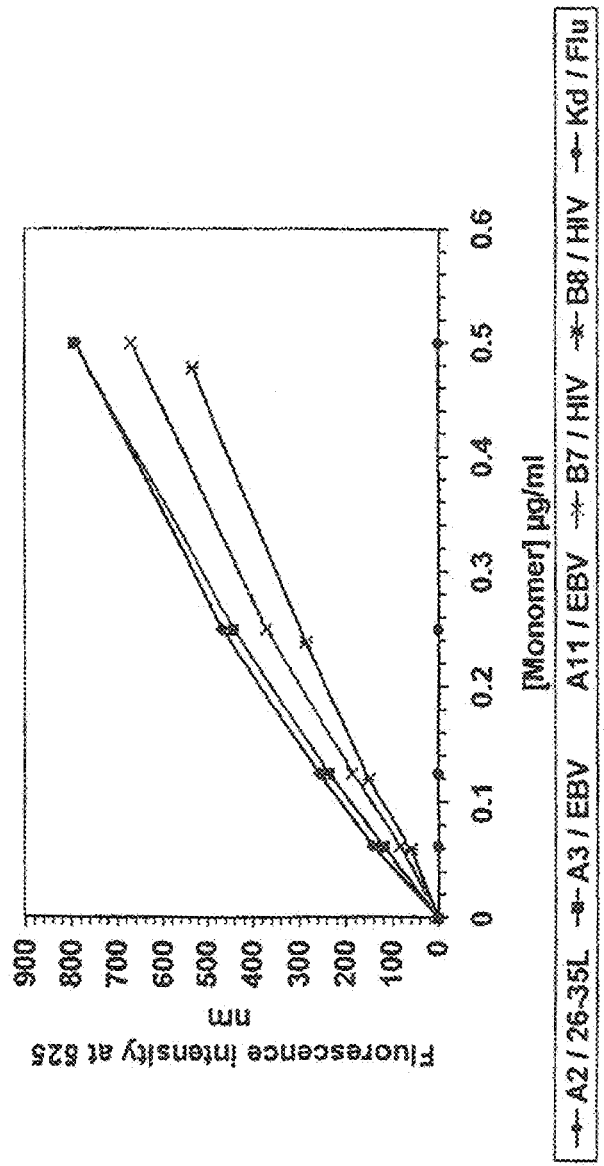
FIG. 8 is a graph showing the specificity of the anti-HLA-class I antibody for various HLA-A and HLA-B alleles.

As shown in FIG. 8, all the human alleles were recognized very well by the same anti-HLA-class I-FITC antibody. No signal was obtained when a human allele was replaced by a mouse allele, indicating that the antibody used is specific for human class I alleles and should be used only in assays involving human alleles. A conformational anti-mouse H-2 antibody was found suitable for use in the assays involving mouse HLA monomers.

Example 4

Measurement of the Peptide-MHC Off Rate

For effective CD8+ T cell responses, class I MHC molecules must bind many peptides of diverse sequence in sufficient abundance for a long period of time. Many tumor cells appear to escape the immune response because antigenic peptides do not bind well to class I MHC molecules that present them. If a peptide does not bind efficiently to the MHC molecule, circulating T cells will not recognize the MHC ternary complex, and cells presenting them will not be eliminated.

Typical half-lives of immunodominant peptides are greater than 20 hours at 37° C. (Stuber, et al., (1994) Eur. J. immunol. 24, 765-768, and Pogue, et al., (1995) Proc. Natl. Acad. Sci. US 92, 8166-8170). From this evidence, a test was developed to use the invention solid phase assay to determine the stability of various complexes at different temperatures, and thus calculate the off rate of the peptides. This parameter is very valuable to know when peptides are used in vaccination for the purpose of eliciting an immune response.

Measurement of the peptide off rate: Monomer HLA-A*0201/Mart-1 2635L was loaded in four different 96-well avidin coated plates. The plate was incubated for two hours under shaking at room temperature. After washing and stripping with citrate phosphate buffer at pH 3.2 the monomer was reconstituted with high affinity peptides HbV core, Mart-1 2635L, with intermediate affinity peptide Mart-1 26-35 as well as the low affinity peptide Mart-1 27-35. Free beta2 microglobulin as well as the anti-HLA-ABC-FITC monoclonal antibody was added at the same time with the peptide. The plates were incubated at 21° C. under shaking overnight. After that, the plates were washed and the level of the fluorescence determined. After this Tris buffer containing the BSA was added to each well and the plates were re-incubated at different temperatures, one plate was incubated at 4° C., one at 21° C., one at 32.5° C. and the last one at 37° C., respectively. Some strips of each plate were washed at different times—4 hours, 24 hours and 48 hours—and the fluorescence at different times was determined.

B0 is the fluorescence determined at time zero. The time zero corresponds to the moment when the plates were washed once the monomer was reconstituted and the plates were placed at different temperatures. B is the fluorescence obtained at each time. After the Ln (Fluorescence Emission) as a function of the time was plotted. Linear regression was calculated and the Half life was calculated as T½=0.69/slope of the curves.

Results of these assays are shown in Table 4 below:

TABLE 4

| Peptide | $T_{1/2\ hours}$ | | | |
|---|---|---|---|---|
| | 4° C. | 21° C. | 32.5° C. | 37° C. |
| HBVcore | 13800 | 493 | 101 | 21.5 |
| 2635L | >1725 | 345 | 98.6 | 22.4 |

TABLE 4-continued

| Peptide | $T_{1/2\ hours}$ | | | |
|---|---|---|---|---|
| | 4° C. | 21° C. | 32.5° C. | 37° C. |
| 2635 | 186 | 20.3 | 2.5 | 1 |
| 2735 | 56.1 | 8.8 | 1.3 | 0.96 |

Figure 10A:
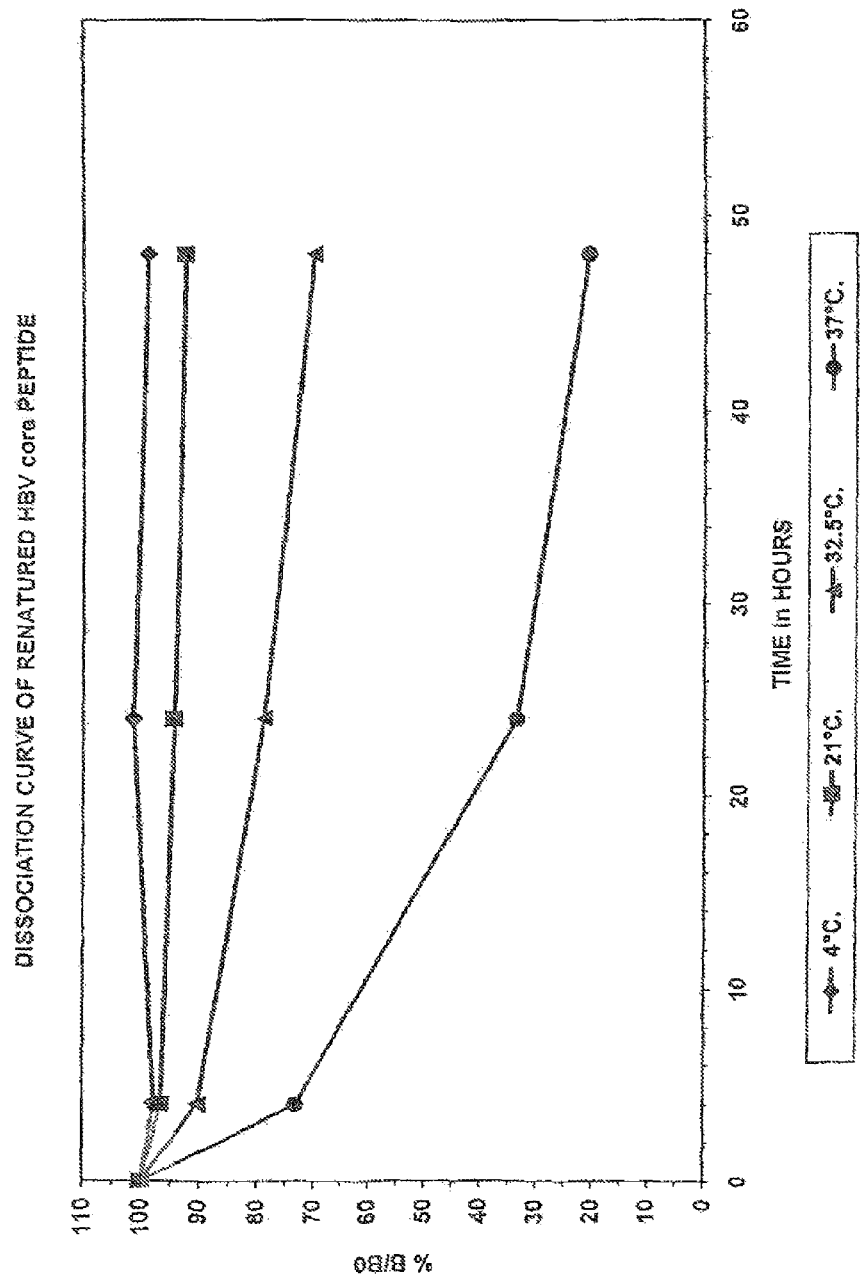
FIGS. 10A-D show graphs of the dissociation curves for renatured peptides (HBV core peptide; 26-35L; 26-35; 27-35, respectively).
Figure 10B:
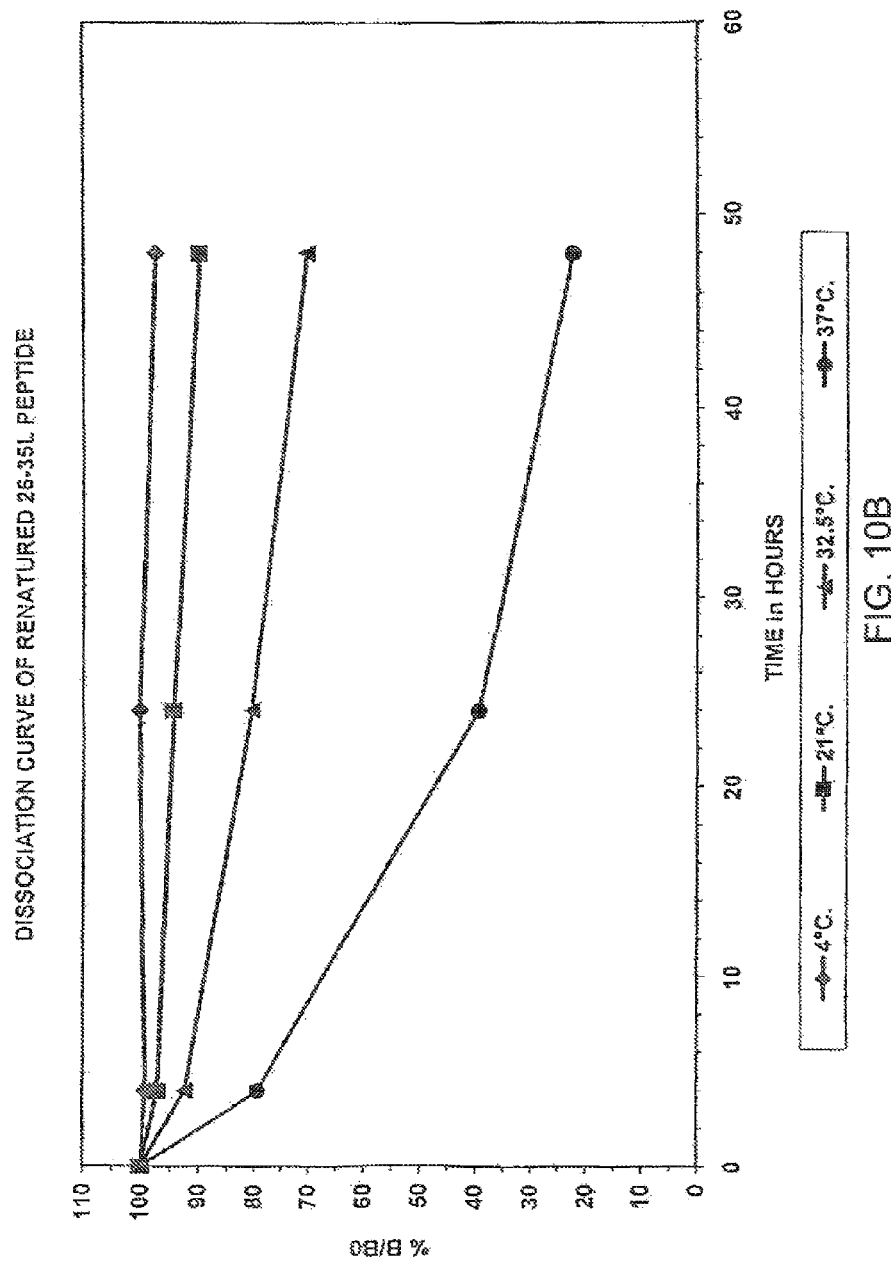
Figure 10C:
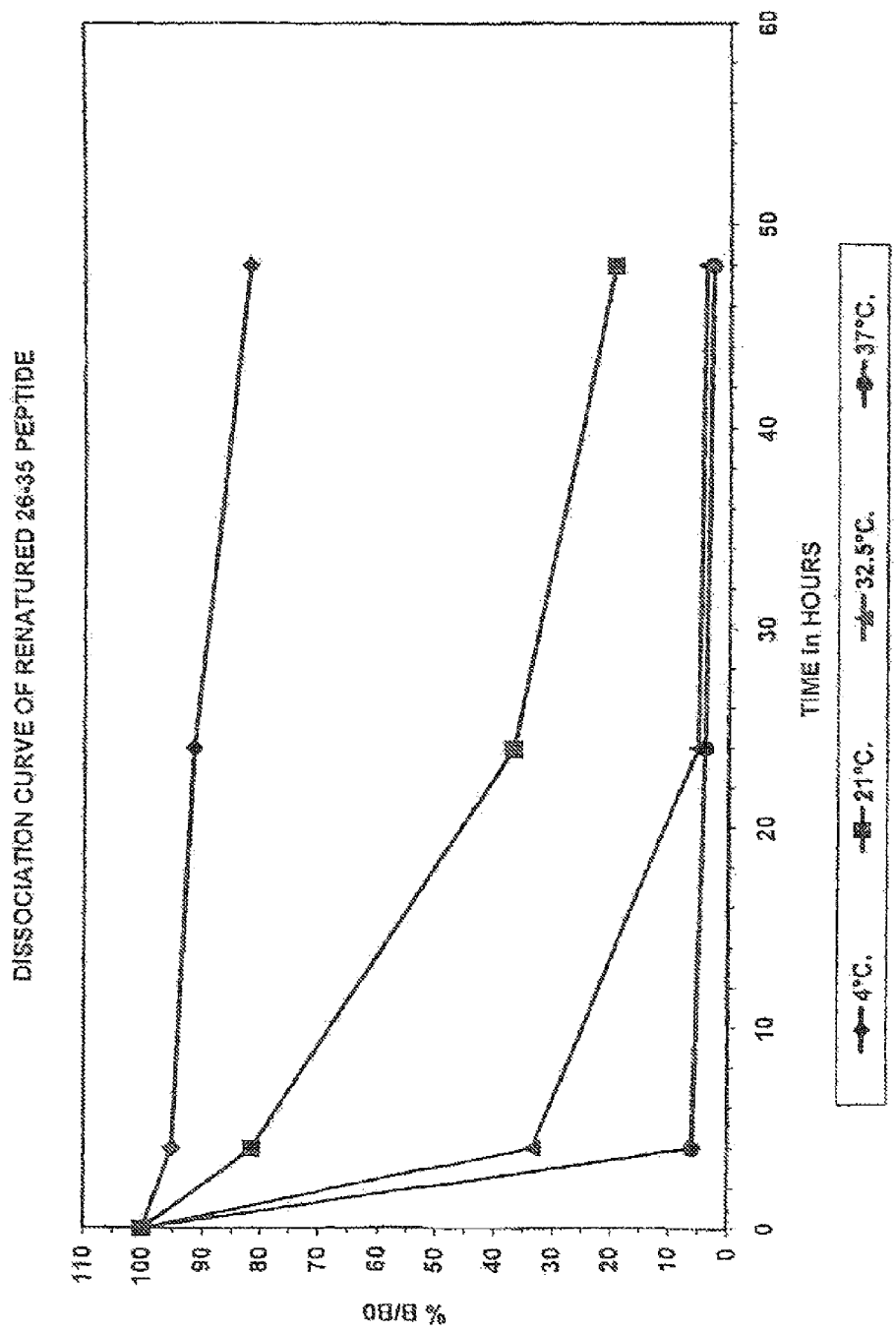
Figure 10D:
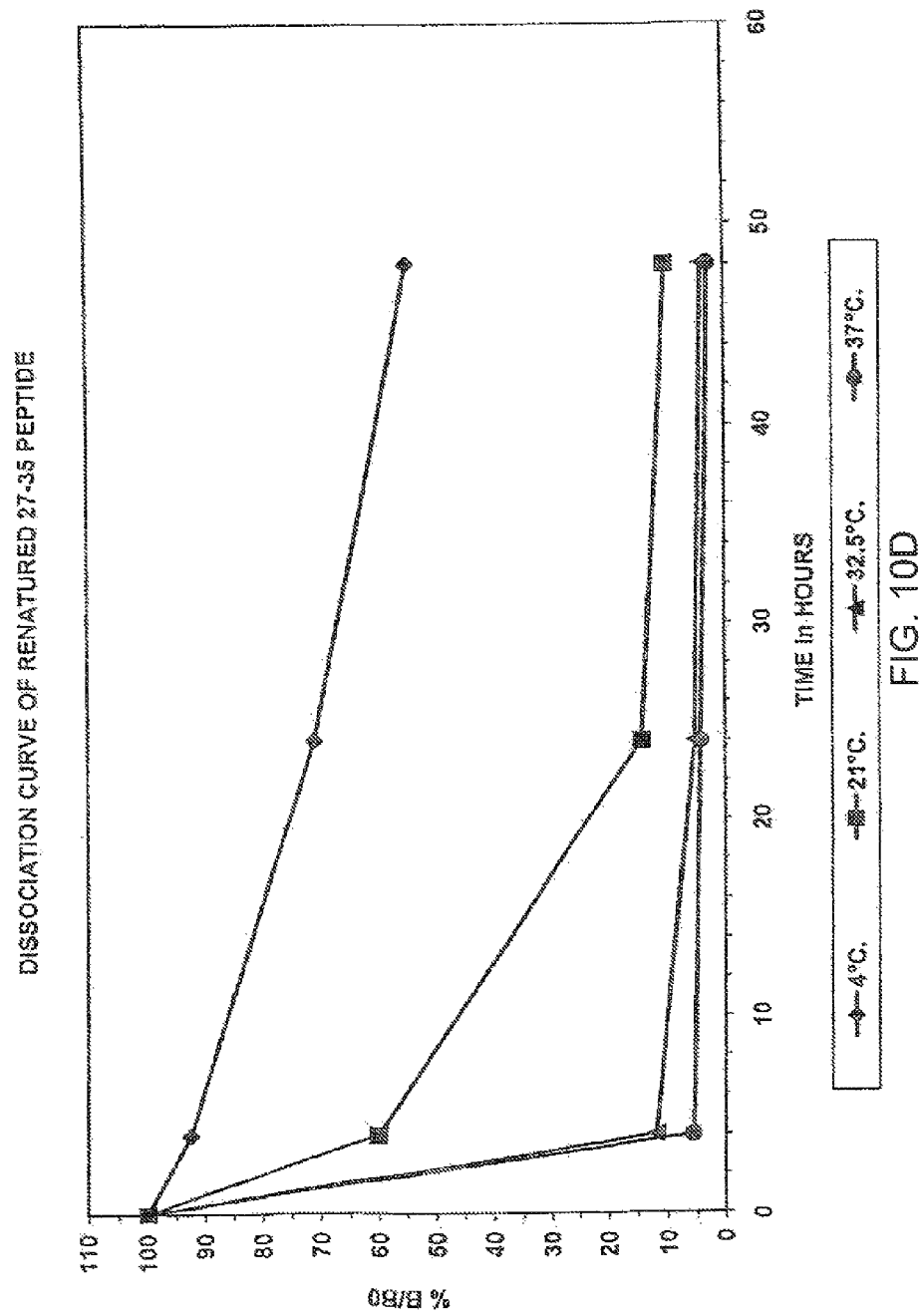
Figure 10E:
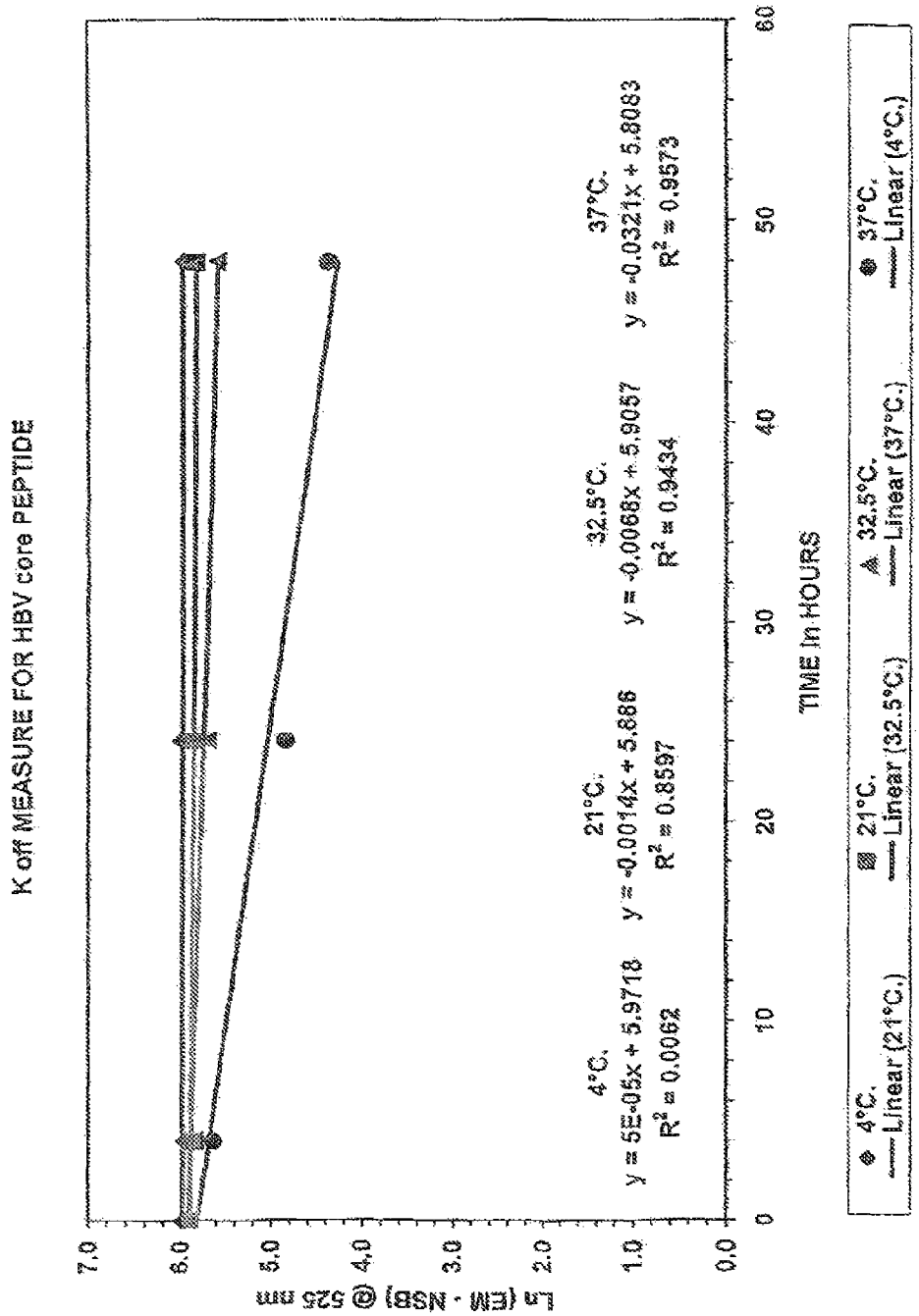
FIGS. 10E-H show graphs of the off rates for peptides HBV core; 26-35L; 26-35; and 27-35, respectively.
Figure 10F:
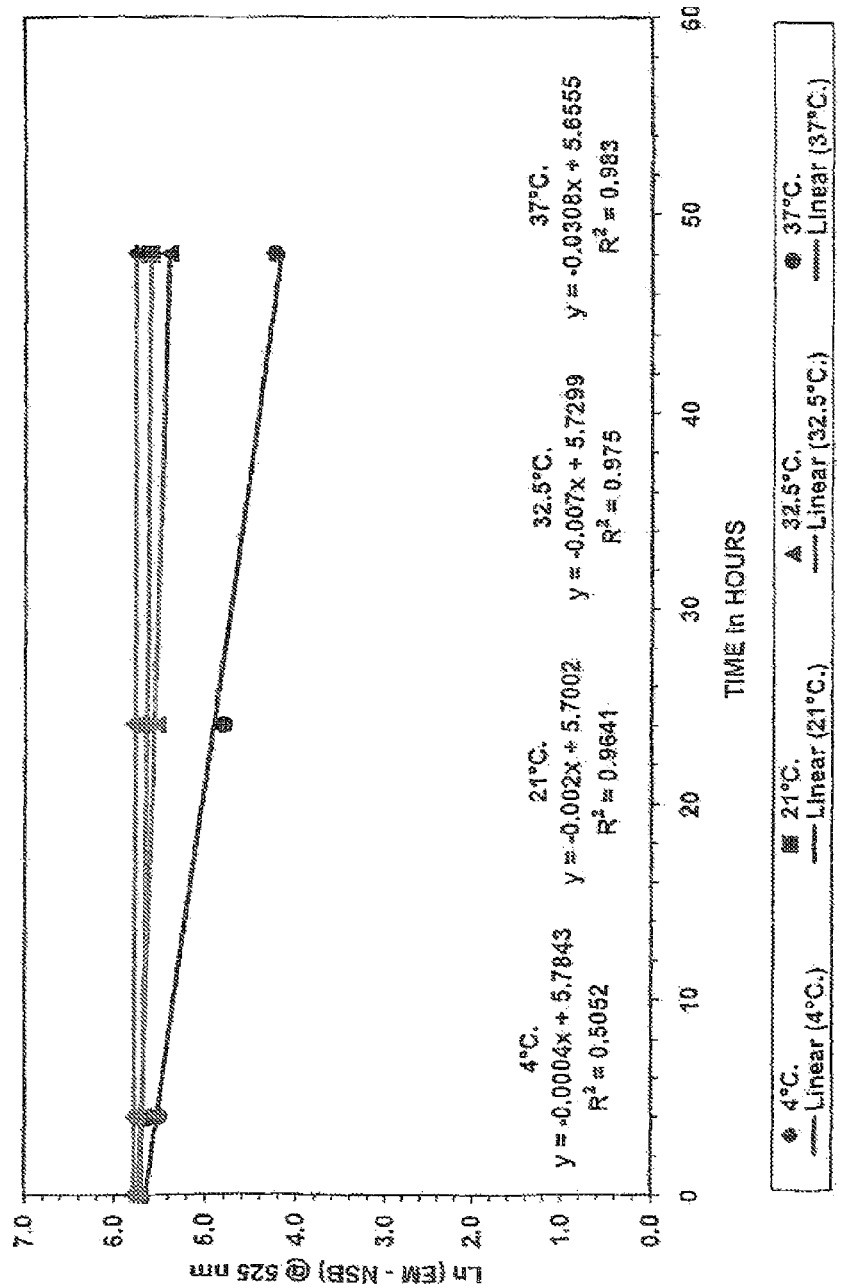
Figure 10G:
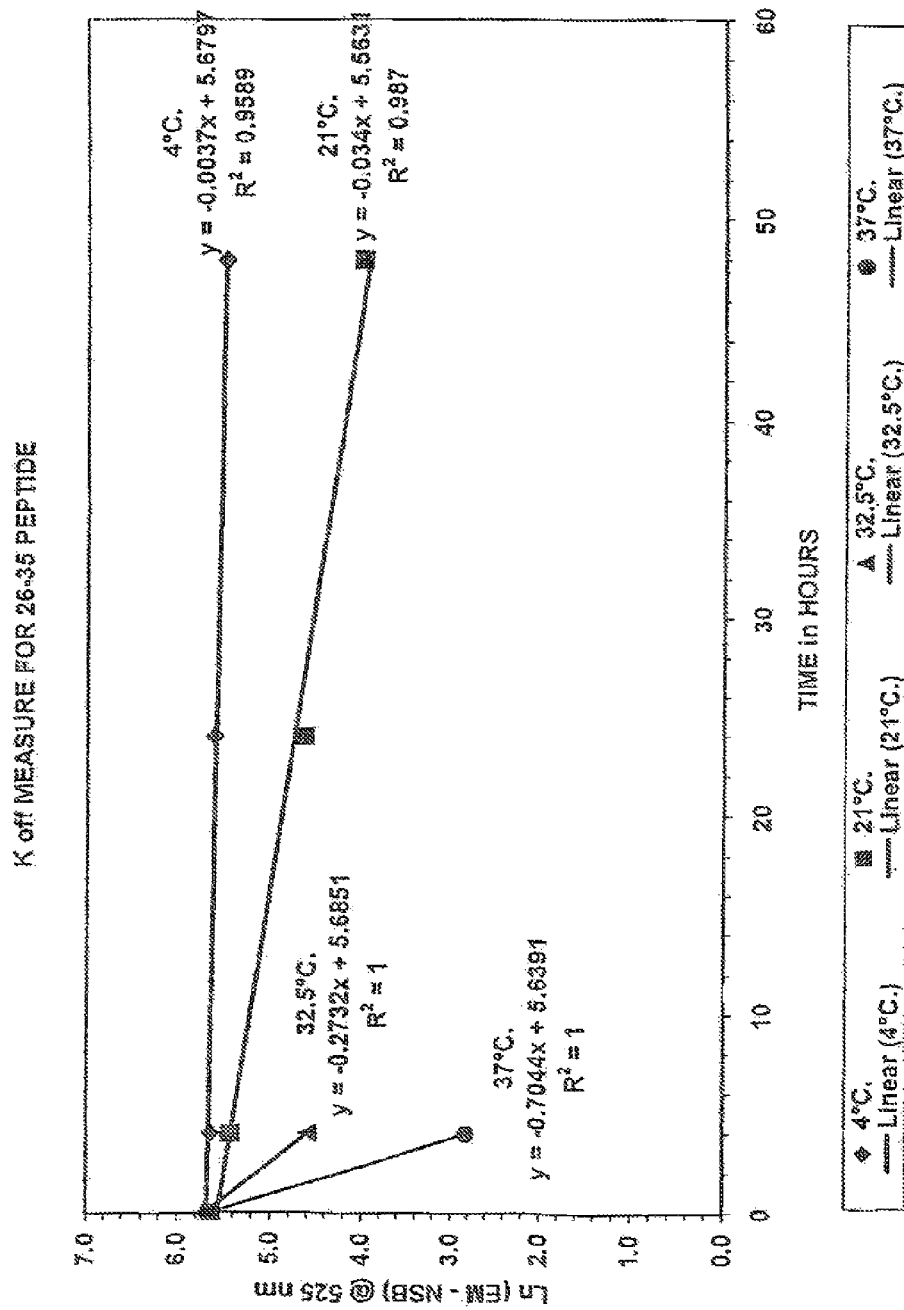
Figure 10H:
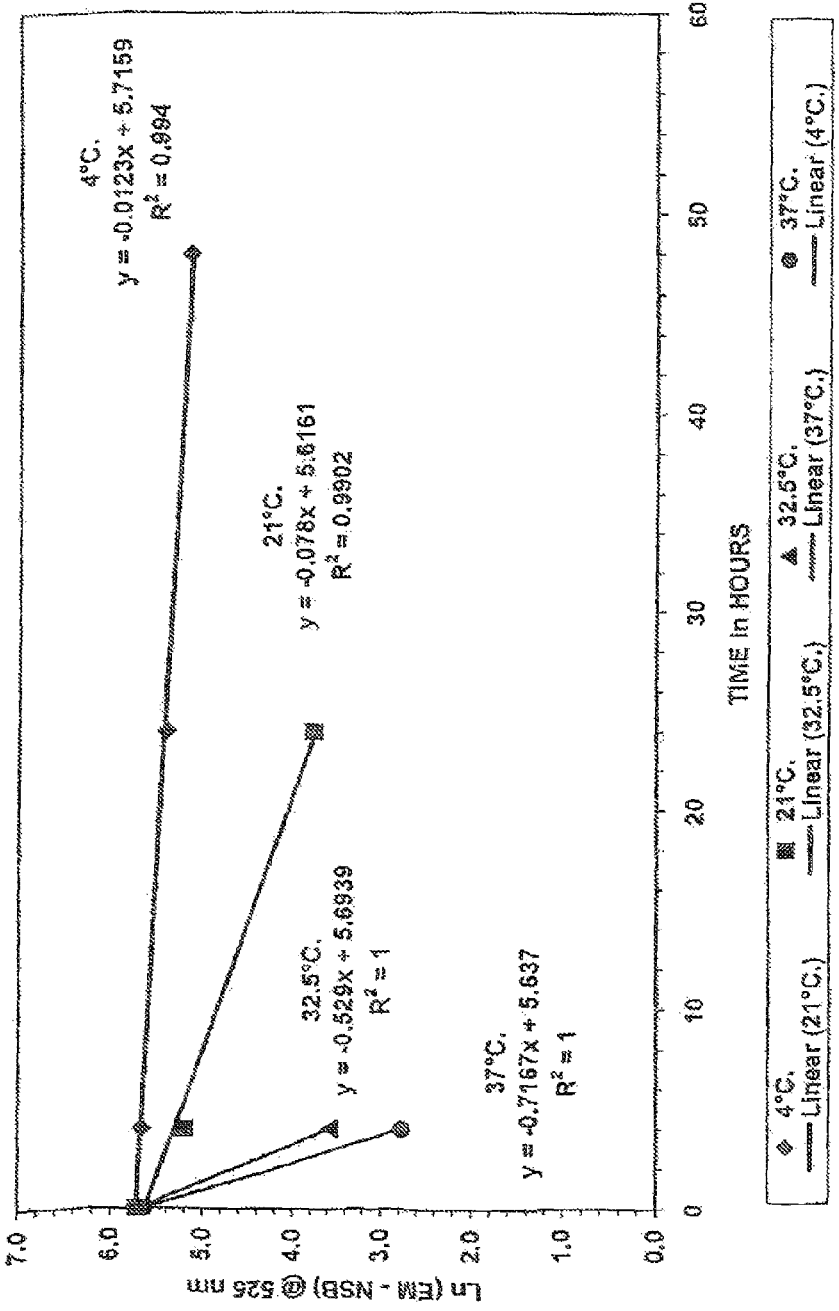
Figure 10I:
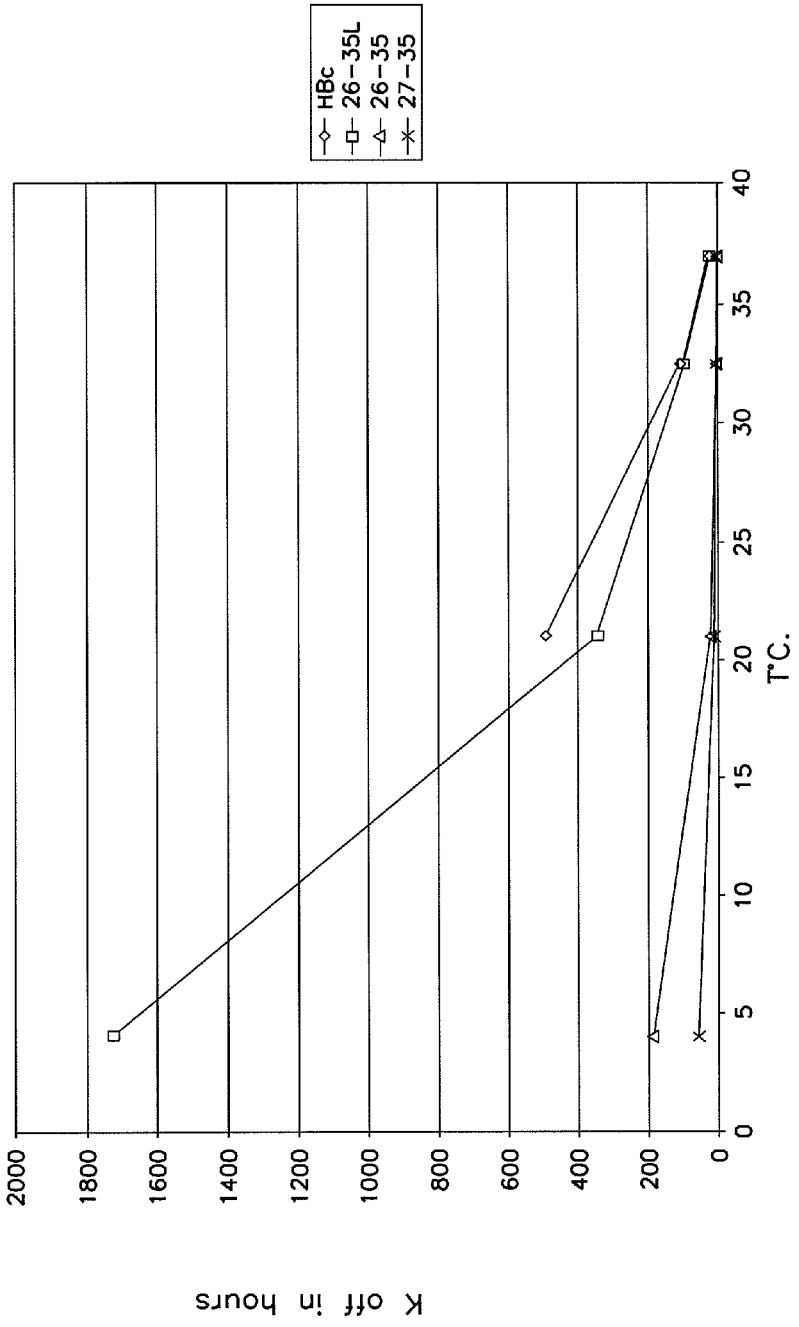
FIG. 10I shows the effect of temperature on monomer dissociation.

It was observed that high affinity peptides, such as HBV core and Mart-1 27-35 had a very good stability at 37° C. and 32.5° C. In contrast, peptide Mart-1 26-35 as well peptide Mart-1 27-35 showed a very high off rate at 37° C. Differences were found also when complexes were incubated at 21° C. These results indicate that the assay can be used to determine the off rate of peptides from the MHC ternary complex (see FIG. 10; FIGS. 10A-D show graphs of the dissociation curves for renatured peptides. FIGS. 10E-H shows graphs of the off rates for peptides. FIG. 10I shows the effect of temperature on monomer dissociation).

Although the invention has been described with reference to the presently preferred embodiment, it should be understood that various modifications can be made without departing from the spirit of the invention. Accordingly, the invention is limited only by the following claims.

What is claimed is:

1. A method to determine binding of a putative MHC binding peptide in a ternary MHC complex with MHC monomer or modified MHC monomer, the method comprising
   (a) exposing a first ternary MHC complex comprising a MHC monomer or modified MHC monomer, peptide, and β2-microglobulin to denaturing conditions comprising a pH of about 2 to about 4 to dissociate the peptide and β2-microglobulin from the MHC monomer or modified MHC monomer to provide a denatured MHC monomer or modified MHC monomer, wherein the MHC monomer or modified MHC monomer is biotinylated and attached to a solid surface comprising avidin or streptavidin through a binding interaction between biotin and the avidin or streptavidin and the denatured MHC monomer or denatured modified MHC monomer remains attached to the solid surface;
   (b) washing the solid surface;
   (c) exposing, under renaturing conditions, the denatured MHC monomer or modified MHC monomer attached to the solid surface to a solution comprising β2-microglobulin and the putative MHC binding peptide;
   (d) determining formation of a second ternary MHC complex comprising the MHC monomer or modified MHC monomer, β2-microglobulin and the putative MHC binding peptide on the solid surface by contacting with an antibody that binds to a ternary MHC complex but not denatured MHC monomer or modified MHC monomer, and detecting binding of the antibody, wherein binding of the antibody indicates formation of the second ternary MHC complex comprising the putative peptide and that the putative MHC binding peptide comprises binding affinity for the MHC monomer or modified MHC monomer.

2. The method of claim 1, wherein the MHC monomer or modified MHC monomer is MHC class I monomer.

3. The method of claim 2, wherein the MHC class I monomer is HLA class I.

4. The method of claim 3, wherein the HLA class I monomer or modified HLA class I monomer is selected from the group consisting of HLA-A, HLA-B, and HLA-C.

5. The method of claim 4, wherein the HLA-A monomer or modified HLA-A monomer is HLA-A*0201, HLA-A*0301, or HLA-A*1101.

6. The method of claim 4, wherein the HLA-B monomer or modified HLA-B monomer is HLA-B*0702 or HLA-B*0801.

7. The method of claim 1, wherein the solid surface is a microtiter plate.

8. The method of claim 1, wherein the antibody is an anti-MHC antibody that binds specifically to a conformational epitope that is present in a ternary MHC complex and not present in the denatured MHC monomer or modified MHC monomer.

9. The method of claim 8, wherein the antibody is monoclonal.

10. The method of claim 9, wherein the monoclonal antibody is produced by hybridoma B9.12.1.

11. The method of claim 9, wherein step (d) further comprises wherein the antibody is provided with a detectable label and the labeled antibody bound to the second ternary MHC complex is detected.

12. The method of claim 1, wherein the renaturing conditions include a pH of from about 7 to about 8.5.

13. The method of claim 1, wherein the putative MHC binding peptide is from about 8 to about 12 amino acids.

14. The method of claim 1, wherein the solid surface is coated with biotinylated protein and the avidin or streptavidin is bound to the biotinylated protein.

15. The method of claim 14, wherein the biotinylated protein is bovine serum albumin (BSA).

* * * * *